United States Patent
Ichikawa et al.

(10) Patent No.: US 8,318,404 B2
(45) Date of Patent: Nov. 27, 2012

(54) SALT AND PHOTORESIST COMPOSITION CONTAINING THE SAME

(75) Inventors: Koji Ichikawa, Toyonaka (JP); Masako Sugihara, Nishinomiya (JP); Hiromu Sakamoto, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 75 days.

(21) Appl. No.: 12/797,466

(22) Filed: Jun. 9, 2010

(65) Prior Publication Data

US 2010/0316952 A1   Dec. 16, 2010

(30) Foreign Application Priority Data

Jun. 12, 2009  (JP) ................. 2009-140958

(51) Int. Cl.
*G03F 7/004* (2006.01)
*G03F 7/30* (2006.01)
*C07C 309/06* (2006.01)
*C07C 309/07* (2006.01)

(52) U.S. Cl. .............. 430/270.1; 430/326; 430/910; 430/921; 430/922; 560/150; 562/42; 562/100; 562/109; 562/113

(58) Field of Classification Search ........... 430/270.1, 430/326, 910, 921, 922; 560/150; 562/42, 562/100, 109, 113
See application file for complete search history.

(56) References Cited

U.S. PATENT DOCUMENTS

| | | | |
|---|---|---|---|
| 7,611,822 B2 | 11/2009 | Takemoto | |
| 7,741,007 B2 * | 6/2010 | Yamaguchi et al. | ....... 430/270.1 |
| 2006/0194982 A1 | 8/2006 | Harada et al. | |
| 2007/0184382 A1 * | 8/2007 | Yamaguchi et al. | ....... 430/270.1 |
| 2008/0076063 A1 | 3/2008 | Yoshida et al. | |
| 2010/0035180 A1 | 2/2010 | Shimada et al. | |
| 2010/0035185 A1 | 2/2010 | Hagiwara et al. | |
| 2010/0062365 A1 | 3/2010 | Shimada et al. | |
| 2010/0119974 A1 * | 5/2010 | Hada et al. | ................. 430/281.1 |

FOREIGN PATENT DOCUMENTS

| | | |
|---|---|---|
| JP | 11-52575 A | 2/1999 |
| JP | 2000-026446 A | 1/2000 |
| JP | 2008-013551 A | 1/2008 |
| JP | 2008-165218 A | 7/2008 |
| WO | WO 2008/099869 A1 | 8/2008 |

* cited by examiner

*Primary Examiner* — John Chu
(74) *Attorney, Agent, or Firm* — Birch, Stewart, Kolasch & Birch, LLP

(57) ABSTRACT

A salt represented by the formula (a1):

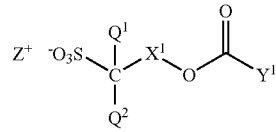

(a1)

wherein $Q^1$ and $Q^2$ each independently represent a fluorine atom or a C1-C4 perfluoroalkyl group,
$X^1$ represents —CO—O—$X^{a1}$— or —CH$_2$—O—$X^{a2}$— wherein $X^{a1}$ and $X^{a2}$ independently each represent a C1-C15 alkylene group and one or more —CH$_2$— in the alkylene group can be replaced by —O— or —CO—,
$Y^1$ represents a C3-C36 alicyclic hydrocarbon group or a C6-C24 aromatic hydrocarbon group, and the alicyclic hydrocarbon group and the aromatic hydrocarbon group can have one or more substituents, and one or more —CH$_2$— in the alicyclic hydrocarbon group can be replaced by —O— or —CO—, and
$Z^+$ represents an organic cation.

8 Claims, No Drawings

SALT AND PHOTORESIST COMPOSITION CONTAINING THE SAME

This nonprovisional application claims priority under 35 U.S.C. §119(a) on Patent Application No. 2009-140958 filed in JAPAN on Jun. 12, 2009, the entire contents of which are hereby incorporated by reference.

FIELD OF THE INVENTION

The present invention relates to a salt suitable for an acid generator and a photoresist composition containing the same.

BACKGROUND OF THE INVENTION

A chemically amplified positive resist composition used for semiconductor microfabrication employing a lithography process contains an acid generator comprising a compound generating an acid by irradiation.

WO 2008/99869 A1 discloses triphenylsulfonium 2-(1-adamantyl)carbonyloxy-1,1-difluoroethanesulfonate and a photoresist composition comprising triphenylsulfonium 2-(1-adamantyl)carbonyloxy-1,1-difluoroethane as an acid generator.

SUMMARY OF THE INVENTION

An object of the present invention is to provide a novel salt suitable for an acid generator and a photoresist composition containing the same.

The present invention relates to the followings:

<1> A salt represented by the formula (a1):

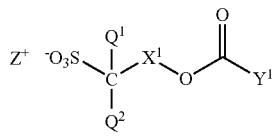
(a1)

wherein $Q^1$ and $Q^2$ each independently represent a fluorine atom or a C1-C4 perfluoroalkyl group, $X^1$ represents —CO—O—$X^{a1}$— or —CH$_2$—O—$X^{a2}$— wherein $X^{a1}$ and $X^{a2}$ independently each represent a C1-C15 alkylene group and one or more —CH$_2$— in the alkylene group can be replaced by —O— or —CO—, $Y^1$ represents a C3-C36 alicyclic hydrocarbon group or a C6-C24 aromatic hydrocarbon group, and the alicyclic hydrocarbon group and the aromatic hydrocarbon group can have one or more substituents, and one or more —CH$_2$— in the alicyclic hydrocarbon group can be replaced by —O— or —CO—, and $Z^+$ represents an organic cation;

<2> The salt according to <1>, wherein $Y^1$ represents a C3-C36 alicyclic hydrocarbon group or a C6-C24 aromatic hydrocarbon group, and one or more hydrogen atoms in the alicyclic hydrocarbon group and the aromatic hydrocarbon group can be replaced by a fluorine atom, a C1-C4 alkyl group, a C1-C4 fluorinated alkyl group, a hydroxyl group, a cyano group, a C2-C8 acyl group, a C2-C8 acyloxy group or a carboxyl group;

<3> The salt according to <1>, wherein $Y^1$ is a group represented by the formula ($Y^1$-1), ($Y^1$-2), ($Y^1$-3), ($Y^1$-4) or ($Y^1$-5):

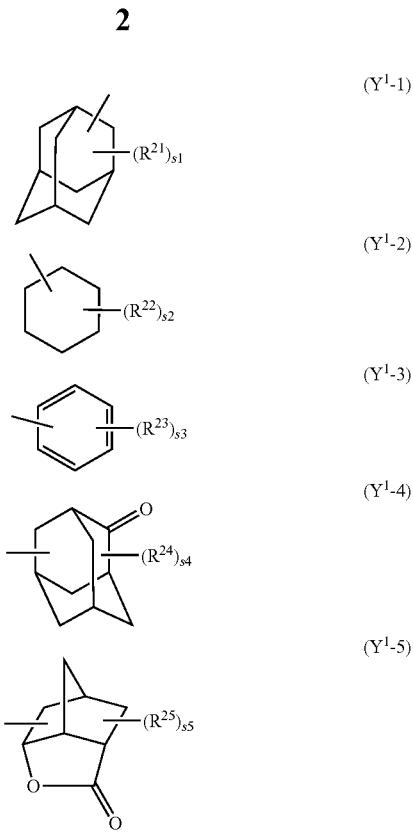

wherein $R^{21}$, $R^{22}$, $R^{23}$, $R^{24}$ and $R^{25}$ are independently in each occurrence a fluorine atom, a C1-C4 alkyl group, a C1-C4 fluorinated alkyl group, a hydroxyl group or a carboxyl group, and s1 represents an integer of 0 to 3, s2 represents an integer of 0 to 3, s3 represents an integer of 0 to 5, s4 represents an integer of 0 to 2, and s5 represents an integer of 0 to 2;

<4> The salt according to any one of <1> to <3>, wherein $Z^+$ is a cation represented by the formula (IXa):

(IXa)

wherein $P^a$, $P^b$ and $P^c$ each independently represent a C1-C30 alkyl group, a C3-C30 alicyclic hydrocarbon group or a C6-C20 aromatic hydrocarbon group, and one or more hydrogen atoms in the alkyl group can be replaced by a hydroxyl group, a C1-C12 alkoxy group or a C3-C12 cyclic hydrocarbon group and one or more hydrogen atoms in the alicyclic hydrocarbon group can be replaced by a hydroxyl group, a C1-C12 alkyl group or a C1-C12 alkoxy group, and one or more hydrogen atoms in the aromatic hydrocarbon group can be replaced by a hydroxyl group, a C1-C12 alkyl group or a C1-C12 alkoxy group, or $P^a$ and $P^b$ are bonded each other to form a ring in which one or more —CH$_2$— can be replaced by —O—, —S—, —SO$_2$— or —CO—;

<5> The salt according to <4>, wherein $P^a$, $P^b$ and $P^c$ each independently represent a C6-C20 aromatic hydrocarbon group, and one or more hydrogen atoms in the aromatic hydrocarbon group can be replaced by a hydroxyl group, a C1-C12 alkyl group or a C1-C12 alkoxy group;

<6> A photoresist composition comprising the salt according to any one of <1> to <5> and a resin comprising a structural unit having an acid-labile group and being insoluble or poorly soluble in an aqueous alkali solution but becoming soluble in an aqueous alkali solution by the action of an acid;

<7> The photoresist composition according to <6>, wherein the photoresist composition further contains a basic compound;

<8> A process for producing a photoresist pattern comprising the following steps (1) to (5):

(1) a step of applying the photoresist composition according to <6> or <7> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention is a salt represented by the formula (a1):

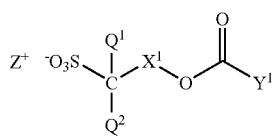

(a1)

wherein $Q^1$ and $Q^2$ each independently represent a fluorine atom or a C1-C4 perfluoroalkyl group, $X^1$ represents —CO—O—$X^{a1}$— or —CH$_2$—O—$X^{a2}$— wherein $X^{a1}$ and $X^{a2}$ independently each represent a C1-C15 alkylene group and one or more —CH$_2$— in the alkylene group can be replaced by —O— or —CO—, $Y^1$ represents a C3-C36 alicyclic hydrocarbon group or a C6-C24 aromatic hydrocarbon group, and the alicyclic hydrocarbon group and the aromatic hydrocarbon group can have one or more substituents, and one or more —CH$_2$— in the alicyclic hydrocarbon group can be replaced by —O— or —CO—, and $Z^+$ represents an organic cation.

The salt of the present invention is preferably a salt represented by the formula (a1) wherein $Q^1$, $Q^2$, $X^1$ and $Z^+$ are the same as defined above, and $Y^1$ represents a C3-C36 alicyclic hydrocarbon group or a C6-C24 aromatic hydrocarbon group, and one or more hydrogen atoms in the alicyclic hydrocarbon group and the aromatic hydrocarbon group can be replaced by a fluorine atom, a C1-C4 alkyl group, a C1-C4 fluorinated alkyl group, a hydroxyl group, a cyano group, a C2-C8 acyl group, a C2-C8 acyloxy group or a carboxyl group.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C15 alkylene group include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, an isopropylene group, a sec-bytylene group and a tert-butylene group.

Examples of —CO—O—$X^{a1}$— include the followings:

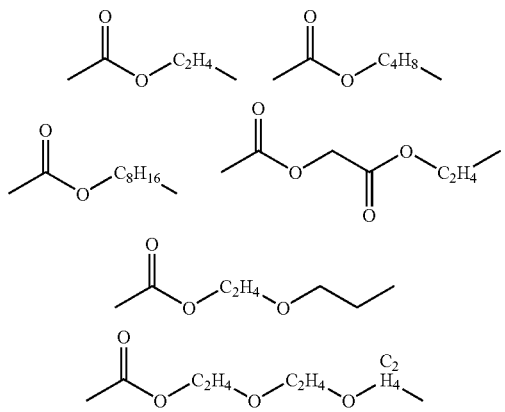

Examples of —CO—O—$X^{a2}$— include the followings:

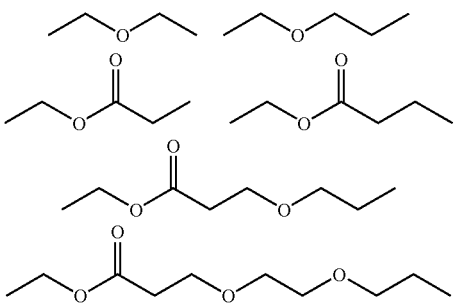

Examples the C3-C36 alicyclic hydrocarbon group and the C6-C24 aromatic hydrocarbon group include groups represented by the formulae (W1) to (W26):

(W1)

(W2)

(W3)

(W4)

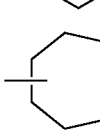
(W5)

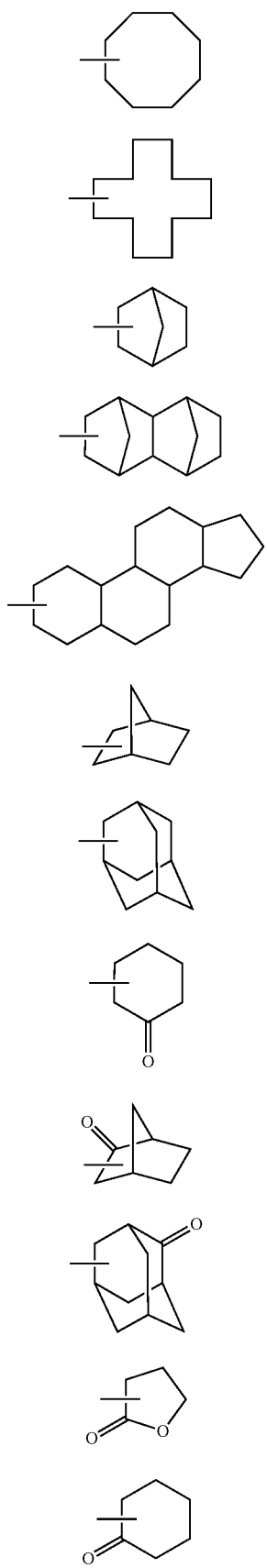
(W6)
(W7)
(W8)
(W9)
(W10)
(W11)
(W12)
(W13)
(W14)
(W15)
(W16)
(W17)
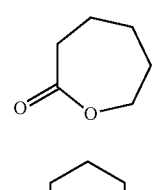
(W18)
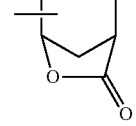
(W19)
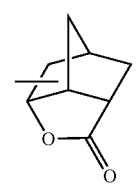
(W20)
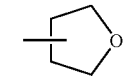
(W21)
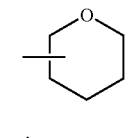
(W22)
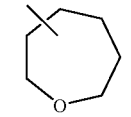
(W23)
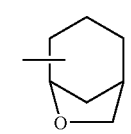
(W24)
(W25)
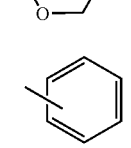
(W26)
The above-mentioned groups represented by the formulae (W1) to (W26) can have one or more substituents. Among them, a group represented by the formula $(Y^1-1)$, $(Y^1-2)$, $(Y^1-3)$, $(Y^1-4)$ or $(Y^1-5)$:
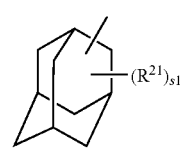
$(Y^1-1)$

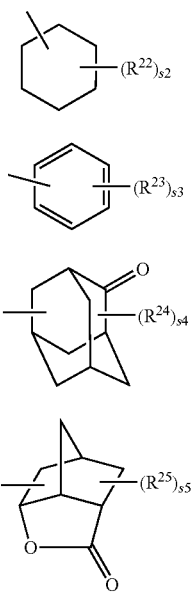

wherein $R^{21}$, $R^{22}$, $R^{23}$, $R^{24}$ and $R^{25}$ are independently in each occurrence a fluorine atom, a C1-C4 alkyl group, a C1-C4 fluorinated alkyl group, a hydroxyl group or a carboxyl group, and s1 represents an integer of 0 to 3, s2 represents an integer of 0 to 3, s3 represents an integer of 0 to 5, s4 represents an integer of 0 to 2, and s5 represents an integer of 0 to 2, is preferable.

Examples of the substituents of the C3-C36 alicyclic hydrocarbon group and the C6-C24 aromatic hydrocarbon group represented by $Y^1$ include a fluorine atom, a C1-C4 alkyl group, a C1-C4 fluorinated alkyl group, a hydroxyl group, a cyano group, a C2-C8 acyl group, a C2-C8 acyloxy group or a carboxyl group.

Examples of the C1-C4 alkyl group include a methyl group, an ethyl group, a propyl group, an isopropyl group, a butyl group, a sec-butyl group and a tert-butyl group. Examples of the C1-C4 fluorinated alkyl group include a trifluoromethyl group, a pentafluoroethyl group, a heptafluoropropyl group, a perfluoroisopropyl group, a nonafluorobutyl group, a perfluoro-sec-butyl group and a perfluoro-tert-butyl group.

Examples of the acyl group include an acetyl group, a propionyl group and a butyryl group. Examples of the acyloxy group include an acetyloxyl group, a propionyloxy group and a butyryloxy group.

$Z^+$ is preferably a sulfonium ion or an iodonium ion, and a sulfonium ion is more preferable.

Examples of $Z^+$ include cations represented by the formulae (IXa), (IXb), (IXc) and (IXd), and a cation represented by the formula (IXa) is preferable.

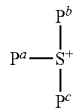
(IXa)

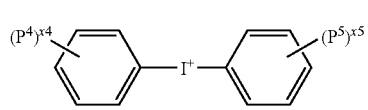
(IXb)

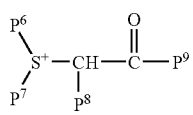
(IXc)

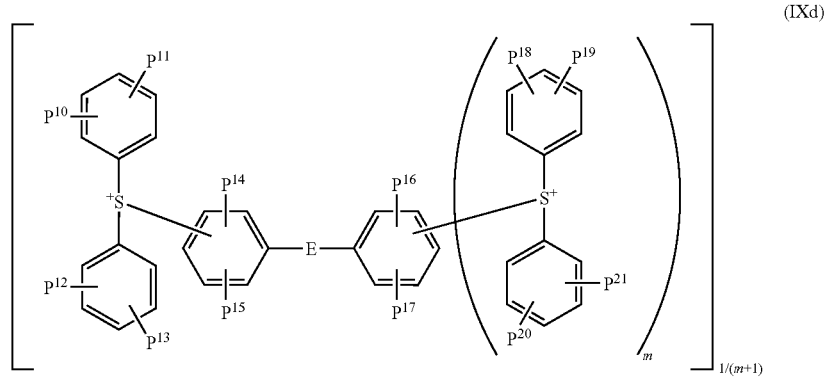
(IXd)

wherein $P^a$, $P^b$ and $P^c$ each independently represent a C1-C30 alkyl group which can have one or more substituents selected from the group consisting of a hydroxyl group, a C3-C12 alicyclic hydrocarbon group and a C1-C12 alkoxy group, a C3-C30 alicyclic hydrocarbon group which can have one or more substituents selected from the group consisting of a hydroxyl group, a C1-C12 alkyl group and a C1-C12 alkoxy group, or a C6-C20 aromatic hydrocarbon group which can have one or more substituents selected from the group consisting of a hydroxyl group, a C1-C12 alkyl group, and a C1-C12 alkoxy group, and $P^4$ and $P^5$ are independently in each occurrence a hydrogen atom, a hydroxyl group, a C1-C12 alkyl group or a C1-C12 alkoxy group, x4 and x5 independently represents an integer of 1 to 5, and $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and one or more —$CH_2$— in the divalent acyclic hydrocarbon group may be replaced by —CO—, —O— or —S—, and $P^8$ represents a hydrogen atom, $P^9$ represents a C1-C12 alkyl group, a C3-C12 cycloalkyl group or a C6-C20 aromatic group which may be substituted, or $P^8$ and $P^9$ are bonded each other to form a divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, E represents a sulfur atom or an oxygen atom and m represents 0 or 1.

Examples of the alkyl group and the alicyclic hydrocarbon group include the same as described above.

Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the cycloalkyl group include a cyclohexyl group and an adamantyl group.

Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the C6-C20 aromatic group include a phenyl group, a tolyl group, a xylyl group, a tert-butylphenyl group and a naphthyl group. Examples of the divalent acyclic hydrocarbon group formed by bonding $P^8$ and $P^9$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (IXa) wherein $P^a$, $P^b$ and $P^c$ each independently represent a C6-C20 aromatic hydrocarbon group which can have one or more substituents selected from the group consisting of a hydroxyl group, a C1-C12 alkyl group, and a C1-C12 alkoxy group, is preferable, and a cation reprsented by the formula (IXaa):

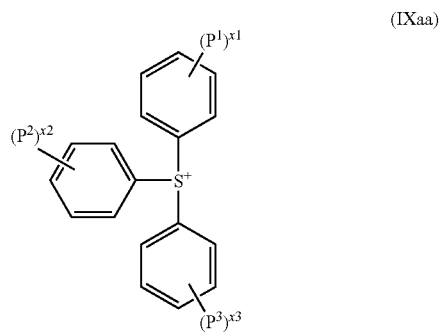

(IXaa)

wherein $P^1$, $P^2$ and $P^3$ are independently in each occurrence a hydrogen atom, a hydroxyl group, a C1-C12 alkyl group or a C1-C12 alkoxy group, and x1, x2 and x3 independently represents an integer of 1 to 5, is more preferable.

Examples of the alicyclic hydrocarbon group include a group having an adamantane structure or an isobornane structure, and a 2-alkyl-2-adamantyl group, a 1-(1-adamantyl)-1-alkyl group and an isobornyl group are preferable.

Examples of the cation represented by the formula (IXaa) include the followings.

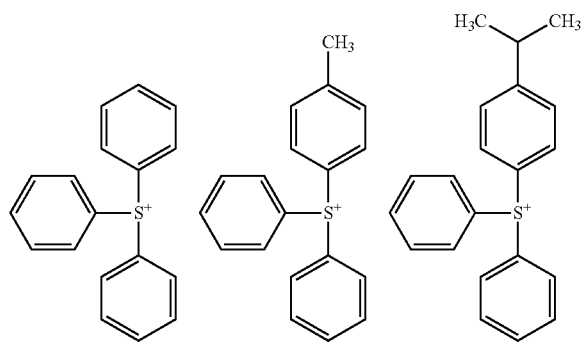

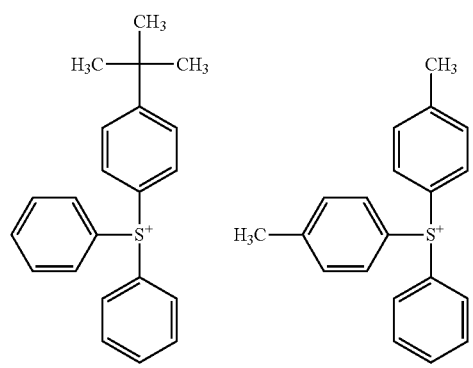

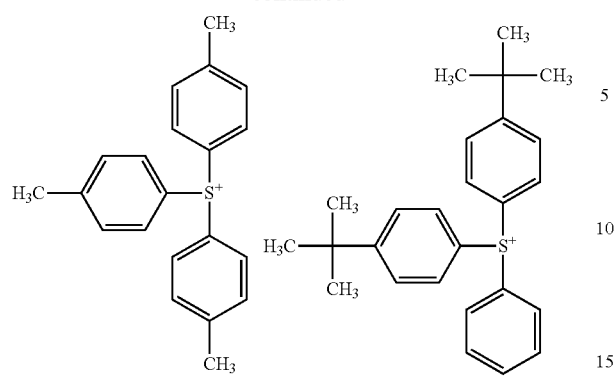
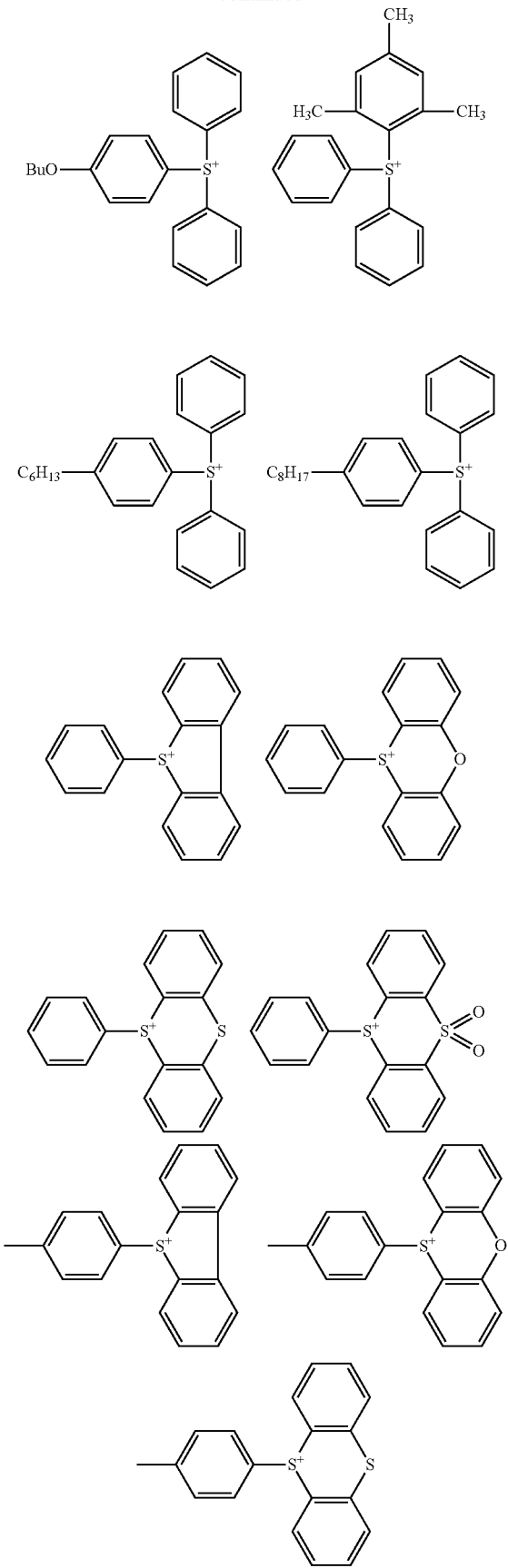

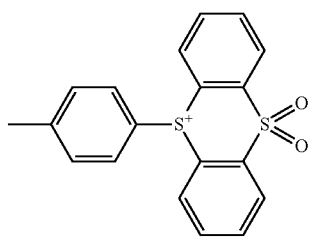
Examples of the cation represented by the formula (IXb) include the followings.
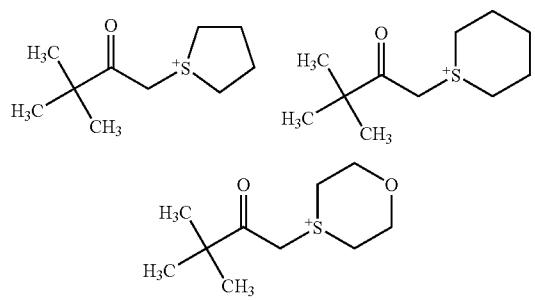
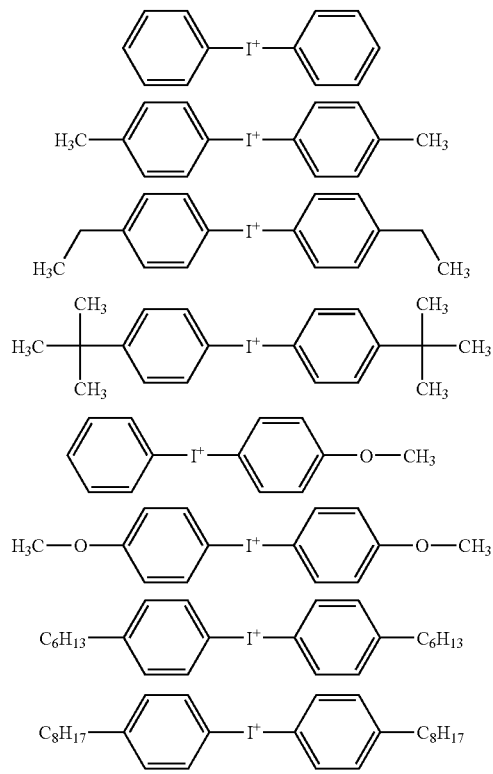
Examples of the cation represented by the formula (IXc) include the followings.
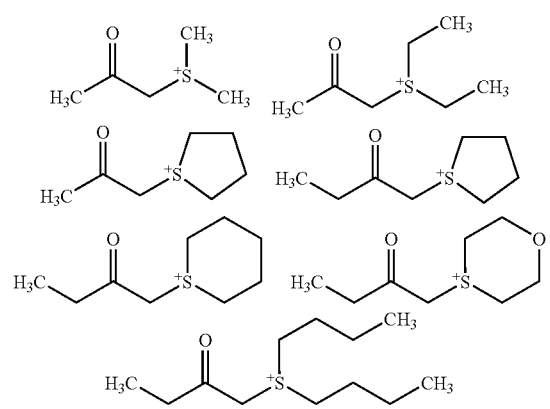
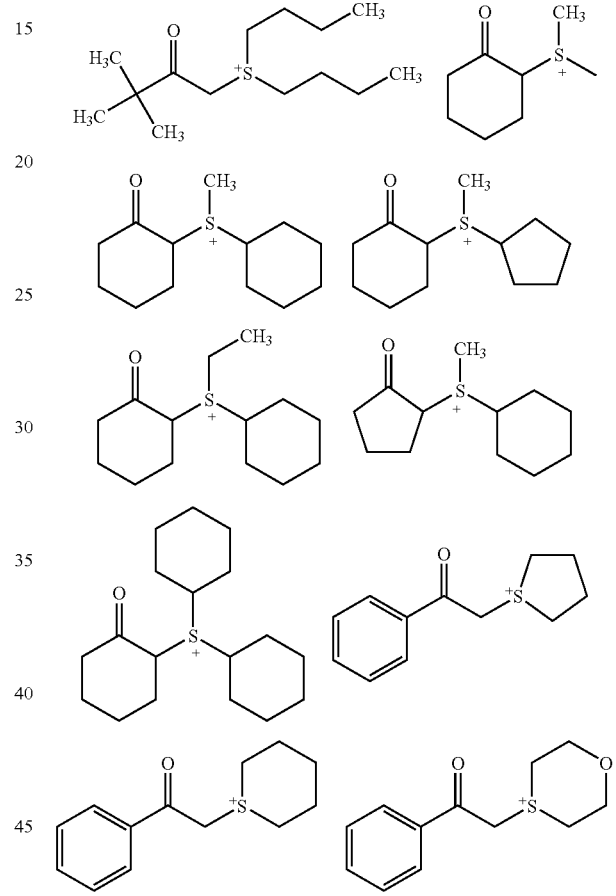
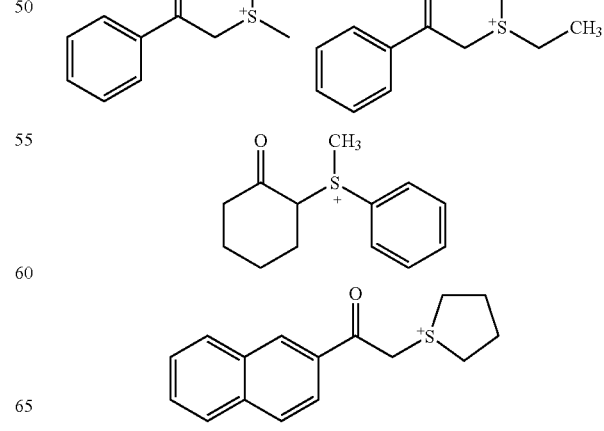

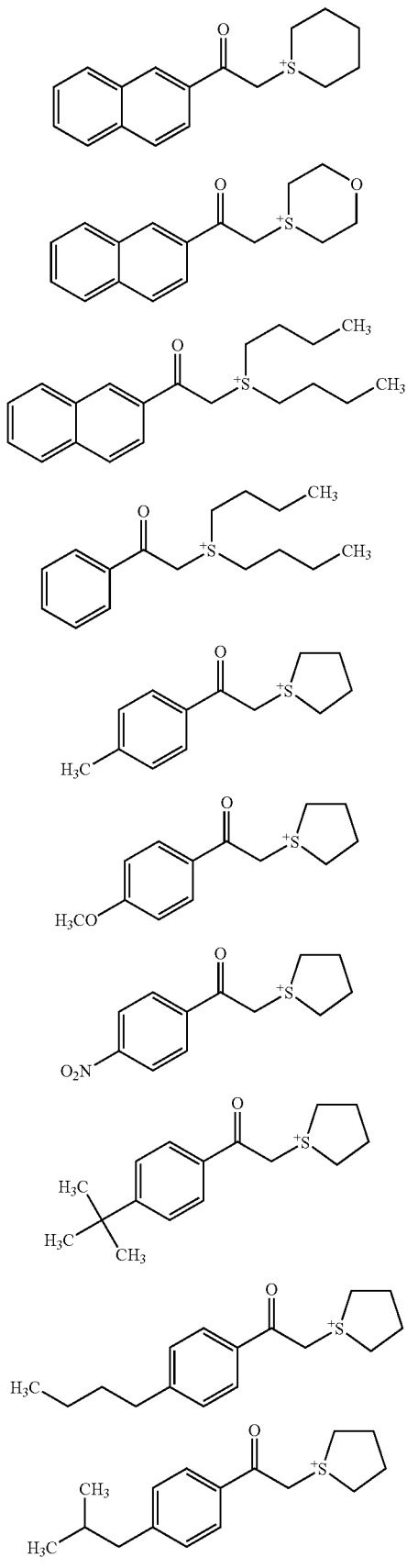
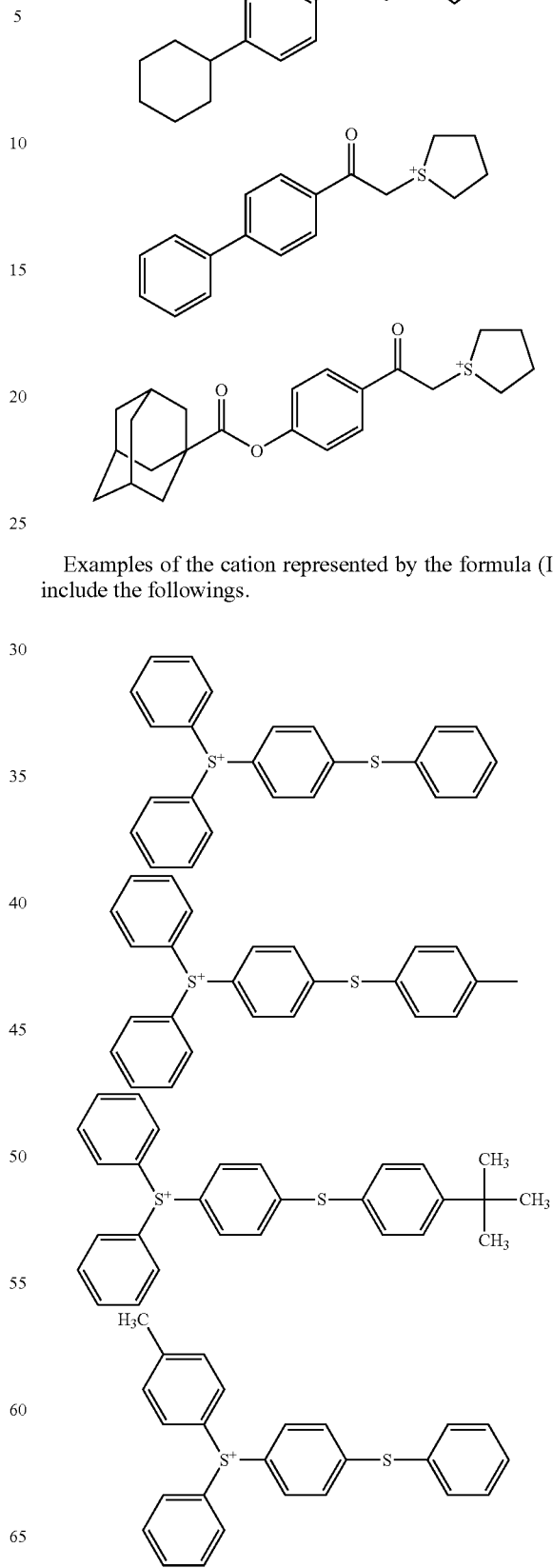
Examples of the cation represented by the formula (IXd) include the followings.

-continued
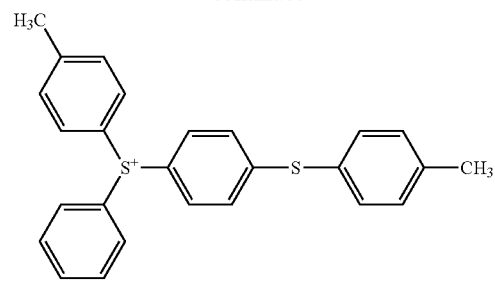
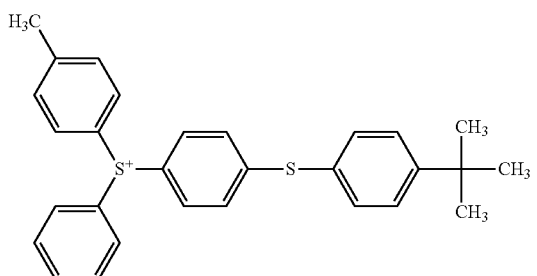
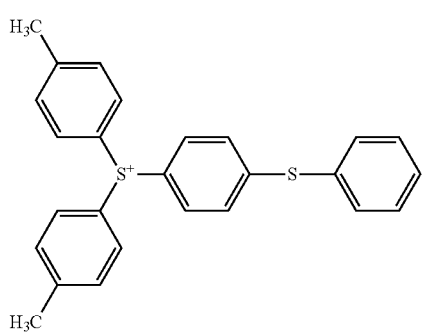
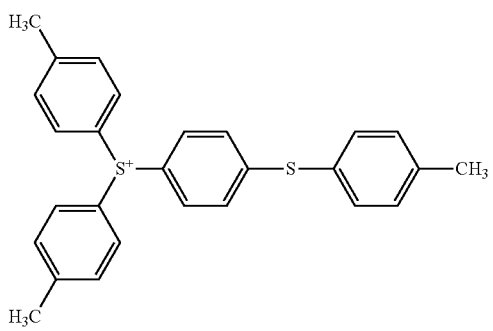
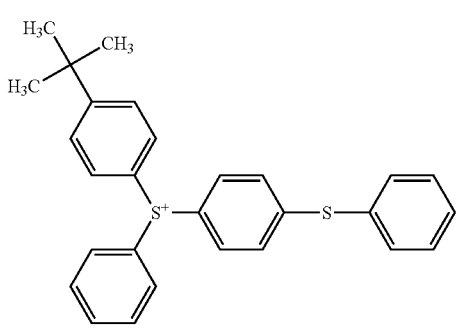
-continued
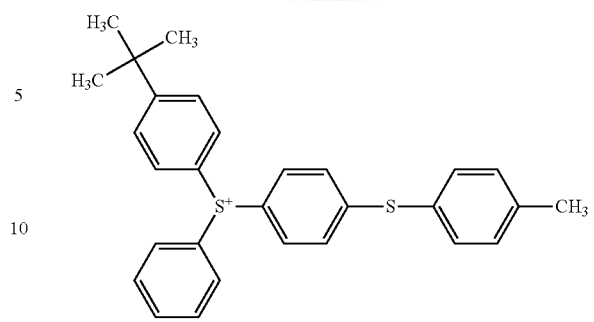
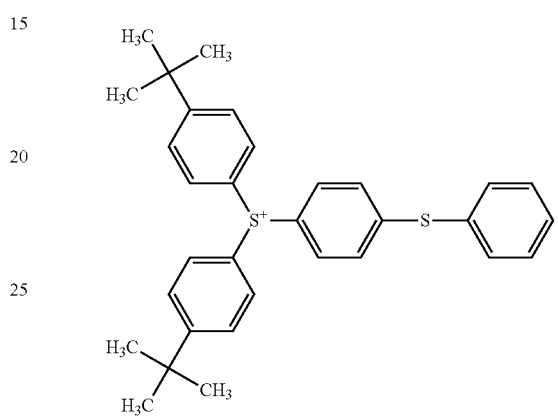
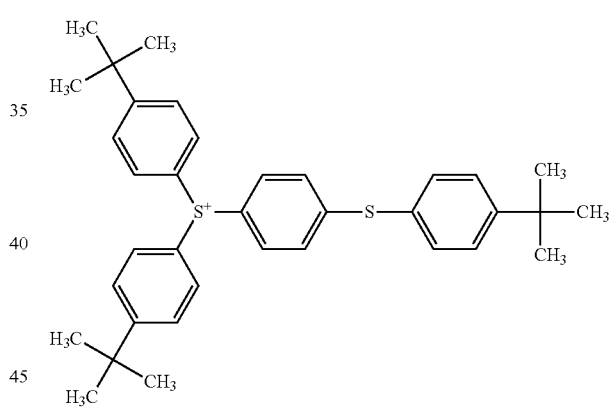
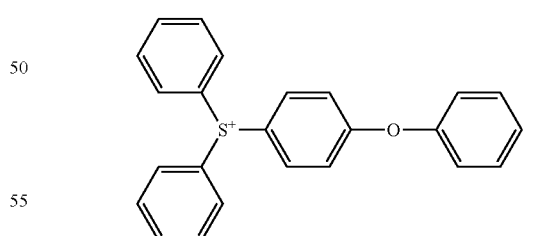
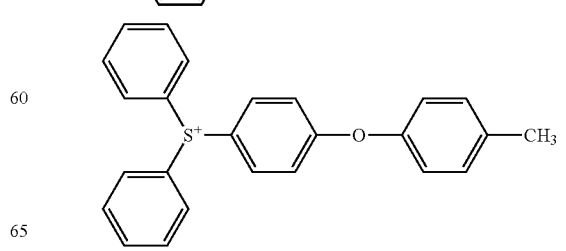

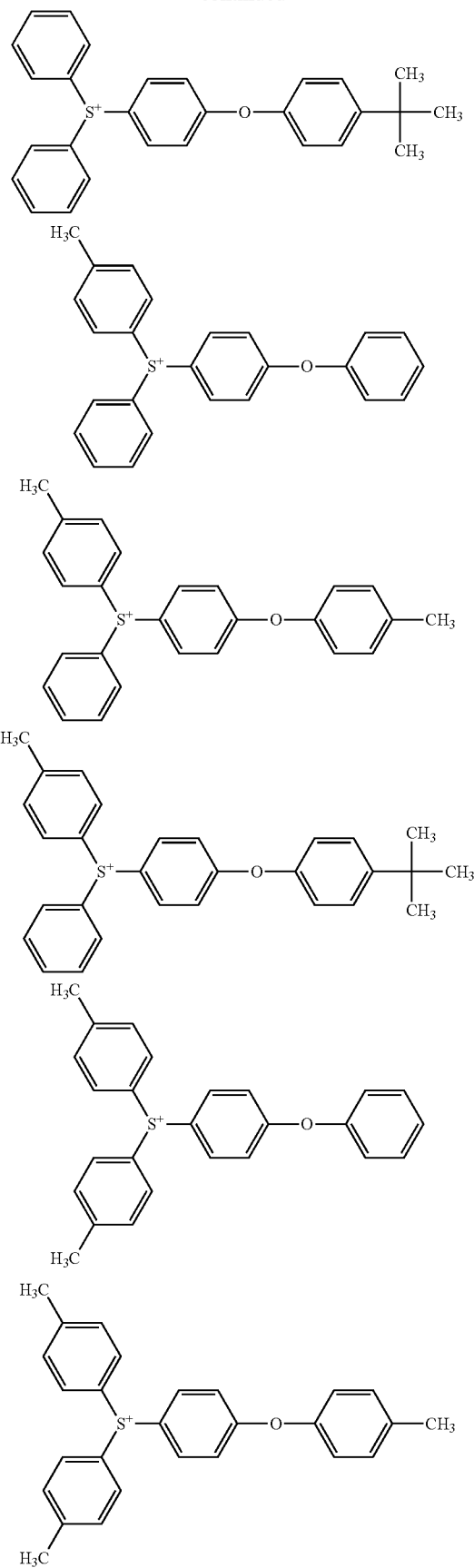
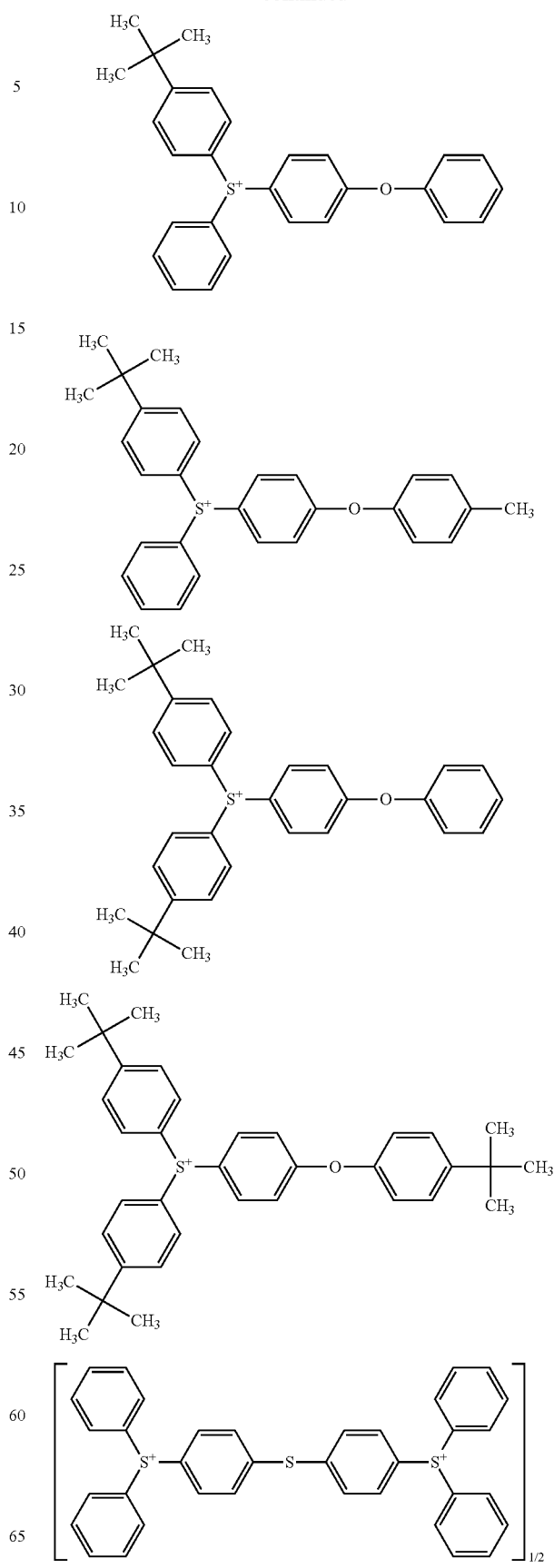

-continued
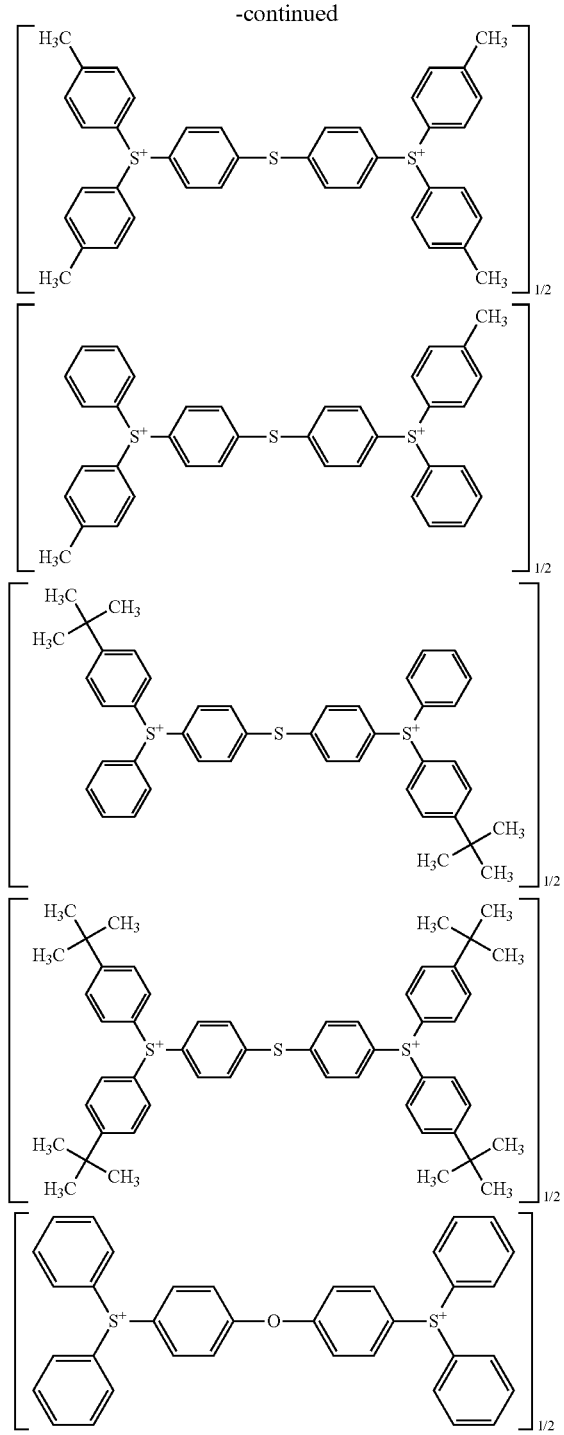
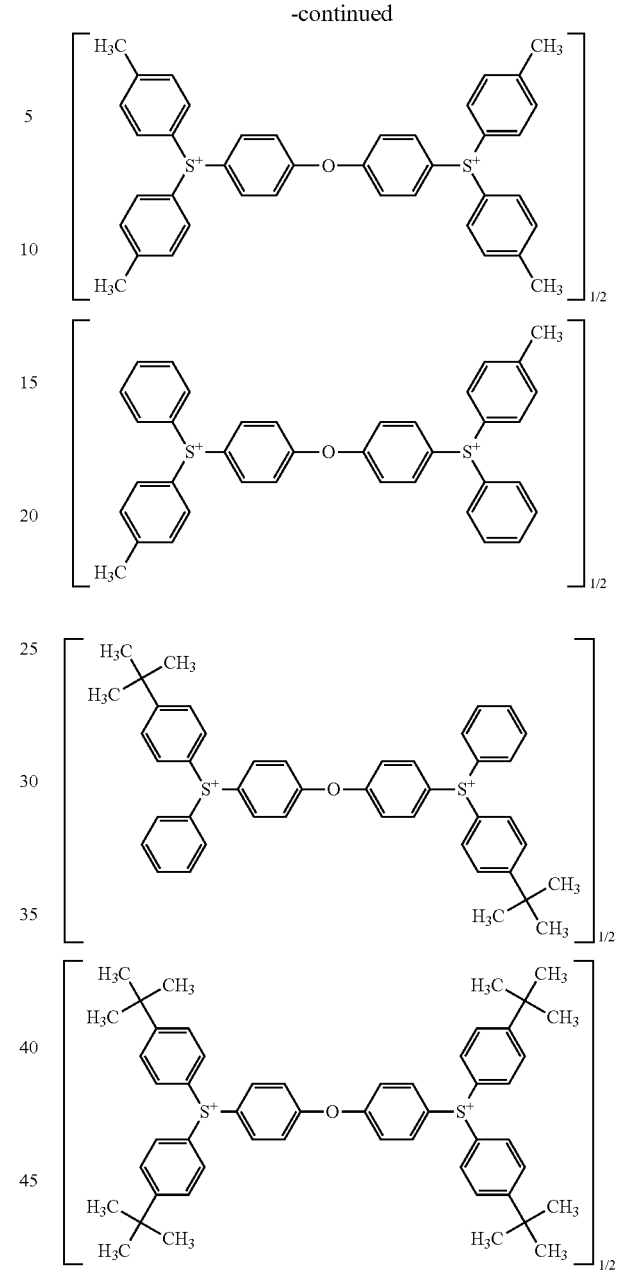
Among them, a sulfonium ion and an iodonium ion are preferable, and a sulfonium ion is more preferable, and an triarylsulfonium ion is especially preferable.
Examples of the salt represented by the formula (a1) include the salts represented by the formulae (I-1) to (I-62):
(I-1)
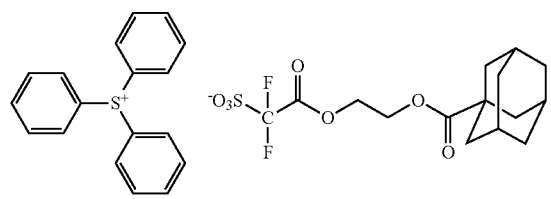
(I-2)
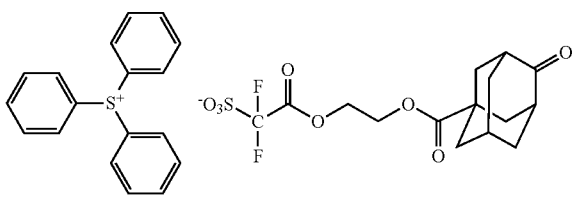

-continued
(I-3)
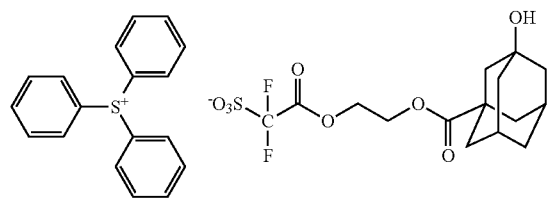
(I-4)
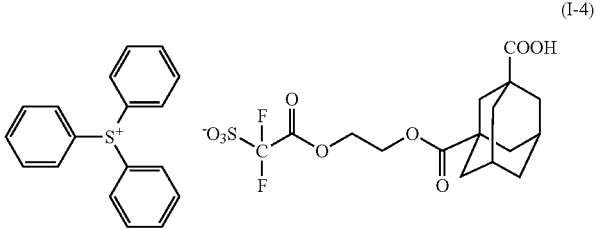
(I-5)
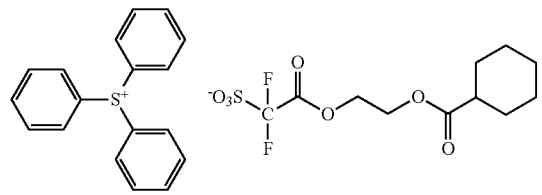
(I-6)
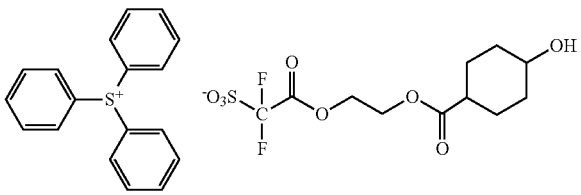
(I-7)
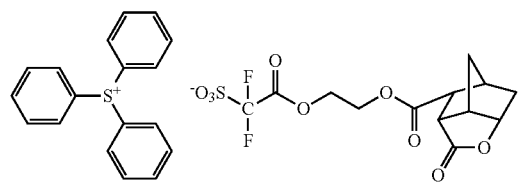
(I-8)
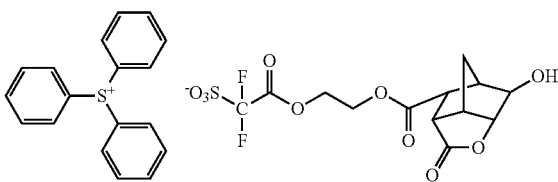
(I-9)
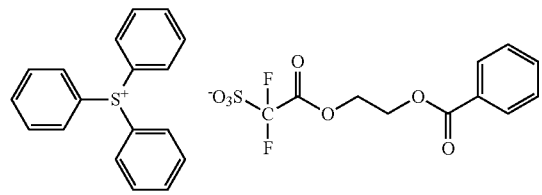
(I-10)
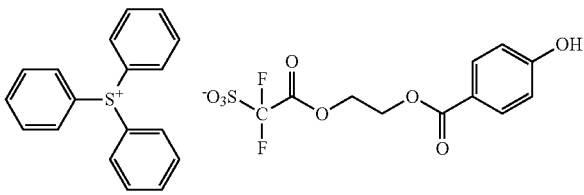
(I-11)
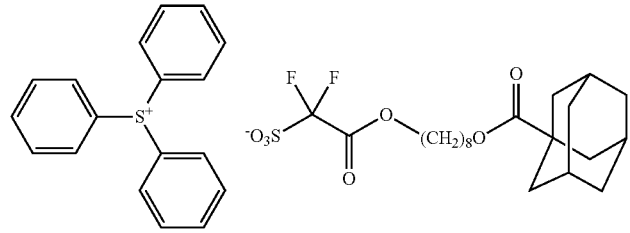
(I-12)
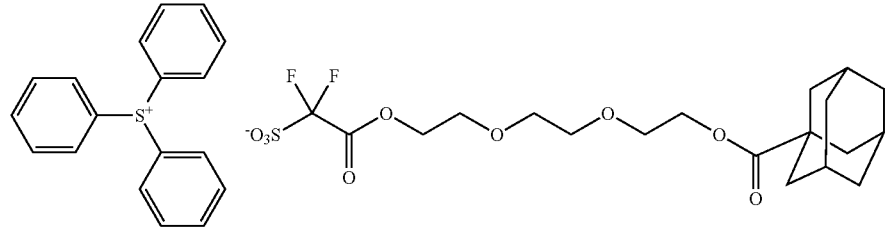
(I-13)
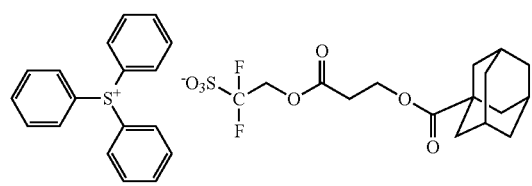
(I-14)
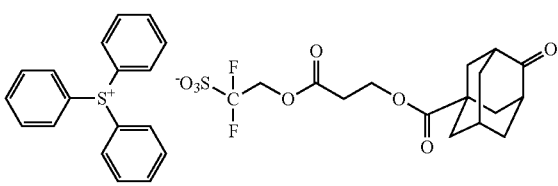

-continued
(I-15)
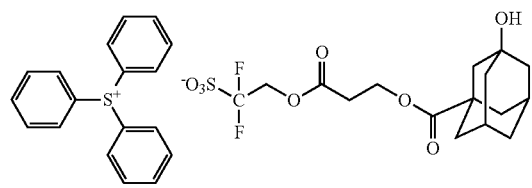
(I-16)
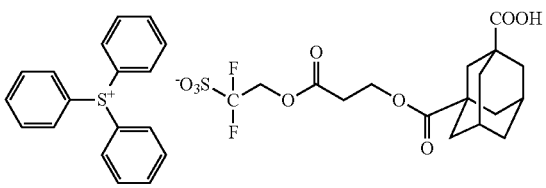
(I-17)
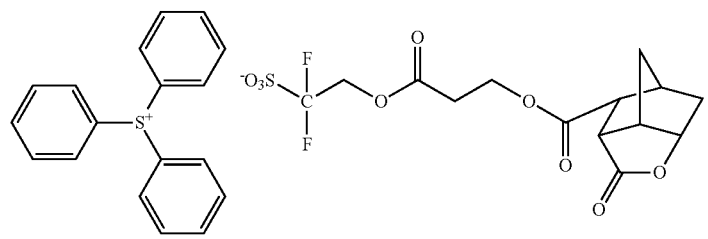
(I-18)
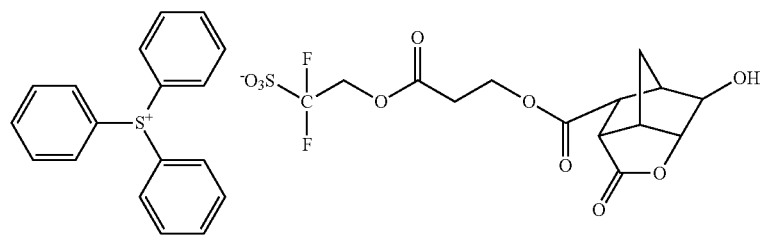
(I-19)
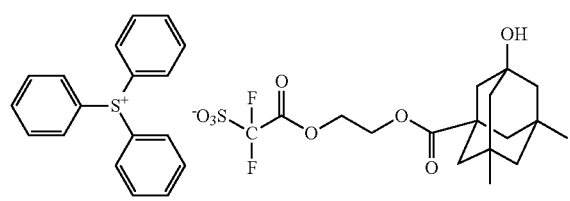
(I-20)
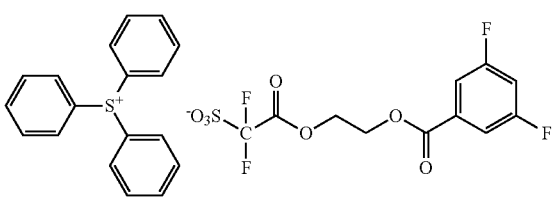
(I-21)
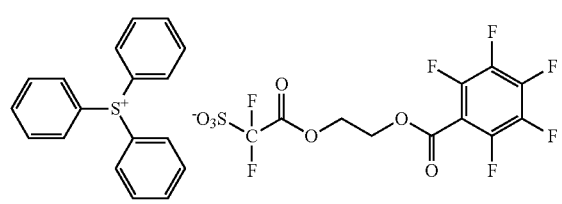
(I-22)
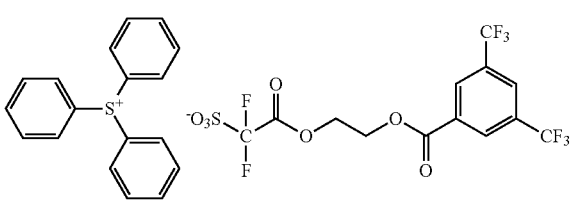
(I-23)
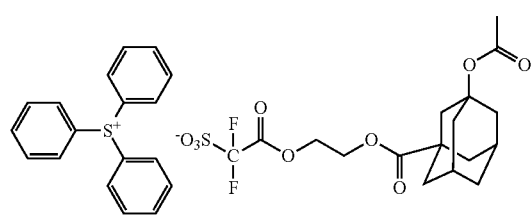
(I-24)
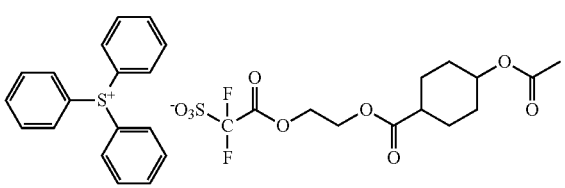
(I-25)
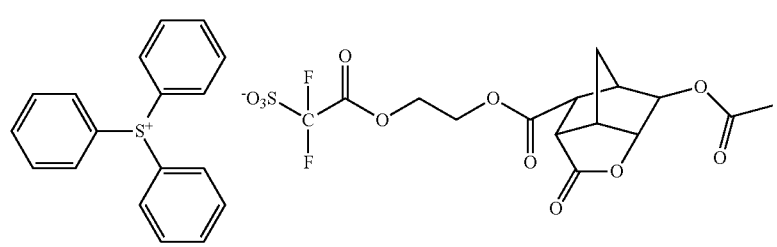

-continued
(I-26)
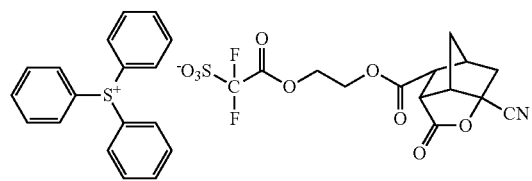
(I-27)
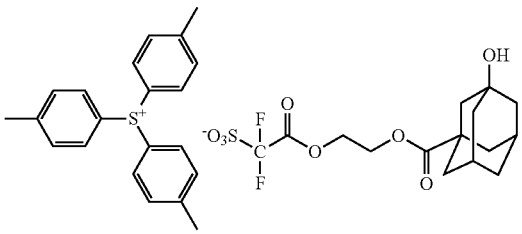
(I-28)
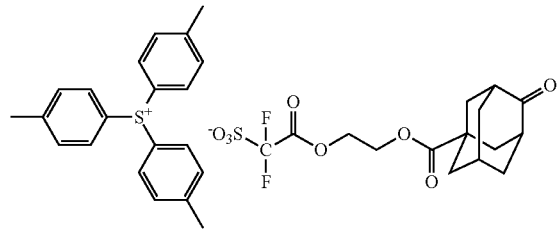
(I-29)
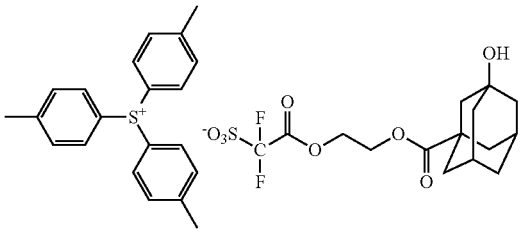
(I-30)
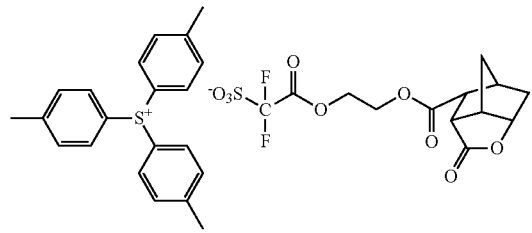
(I-31)
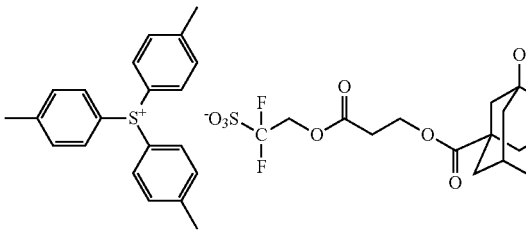
(I-32)
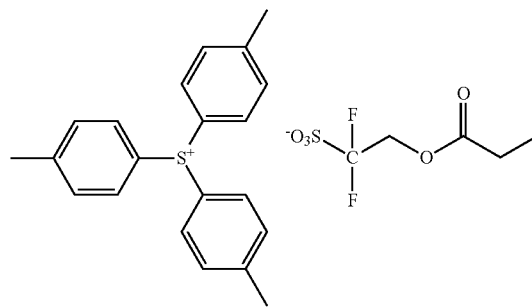
(I-33)
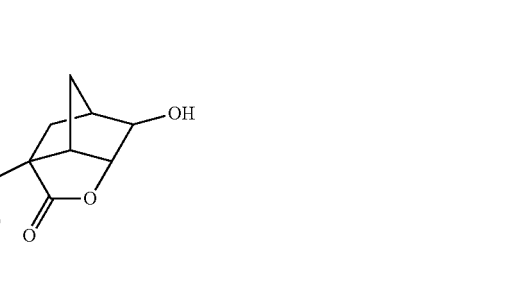
(I-34)
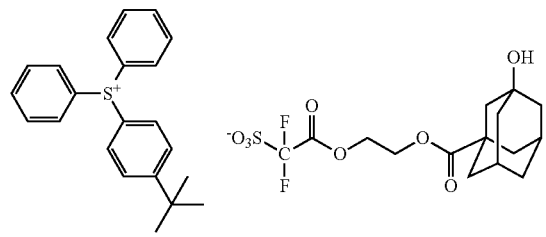
(I-35)
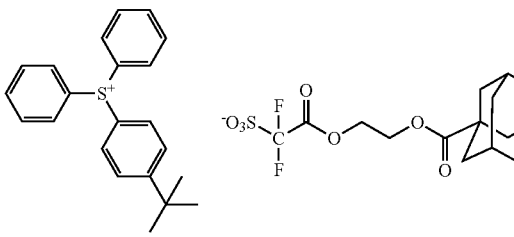
(I-36)
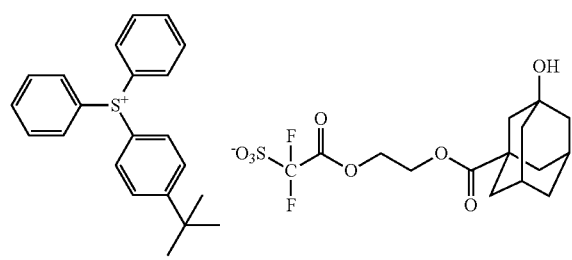
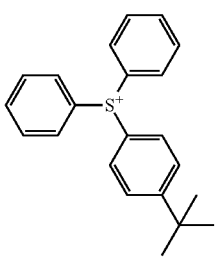

(I-37)
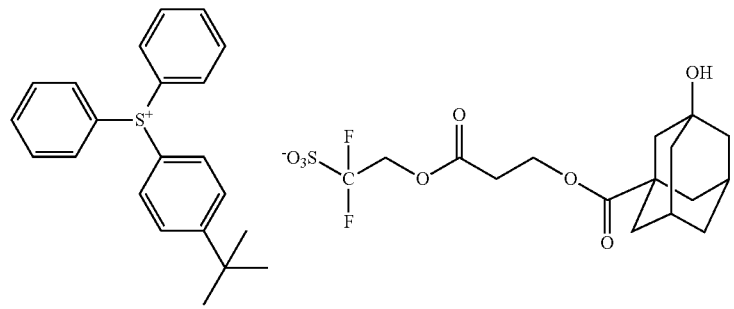
(I-38)
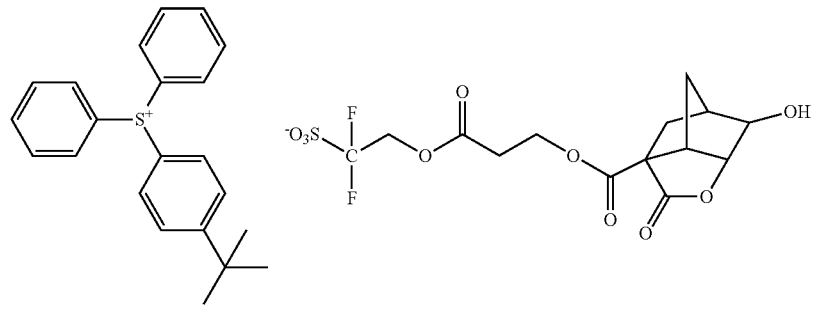
(I-39)
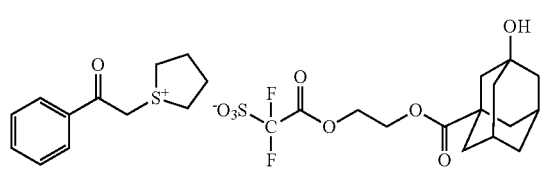
(I-40)
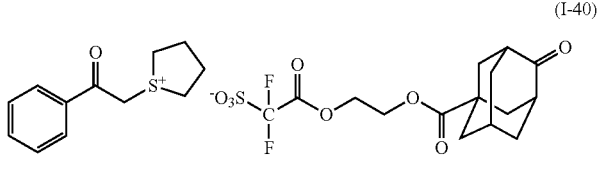
(I-41)
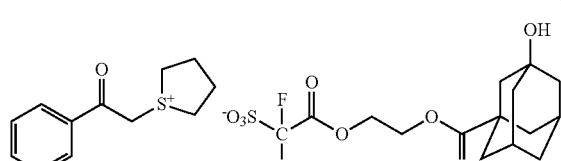
(I-42)
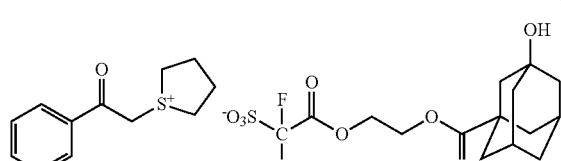
(I-43)
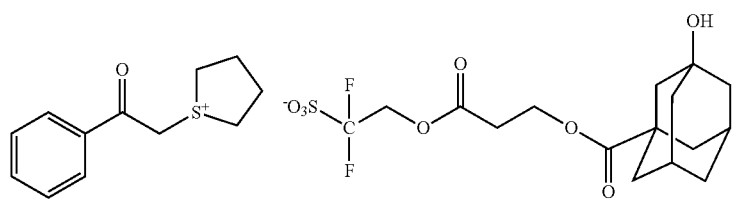
(I-44)
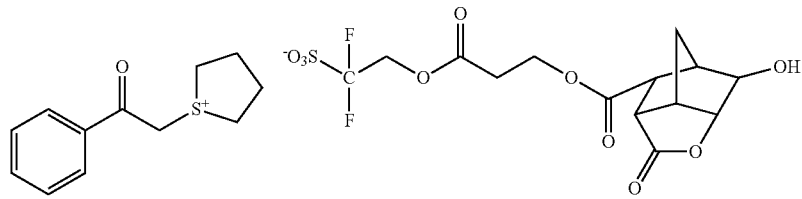
(I-45)
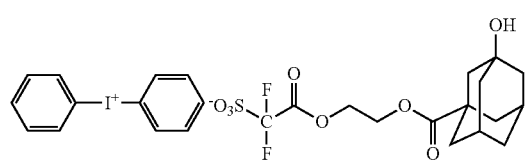
(I-46)
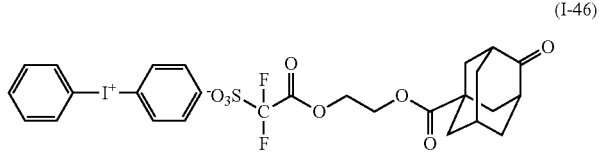

-continued
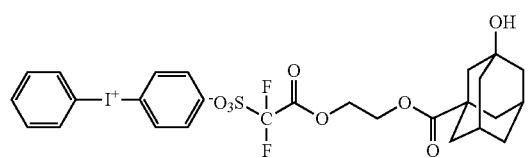
(I-47)
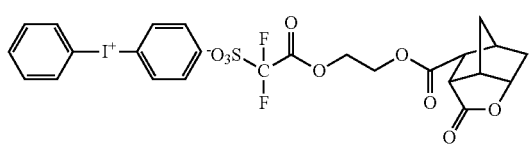
(I-48)
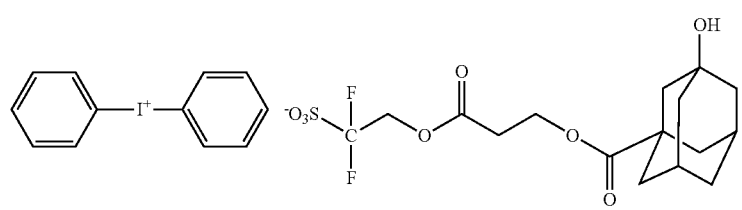
(I-49)
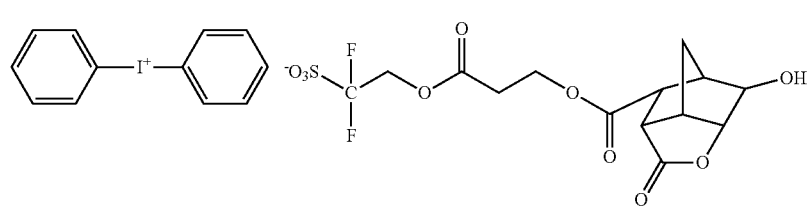
(I-50)
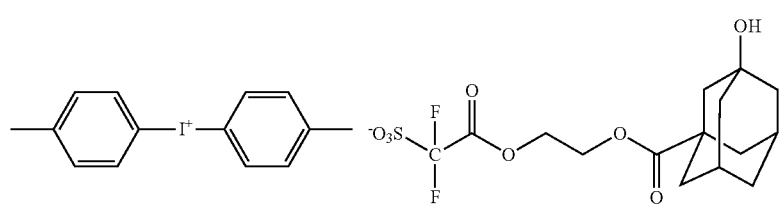
(I-51)
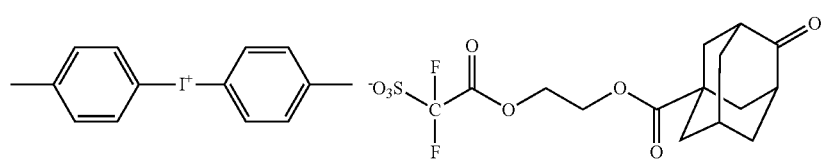
(I-52)
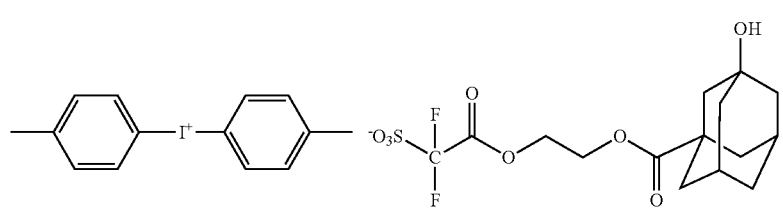
(I-53)
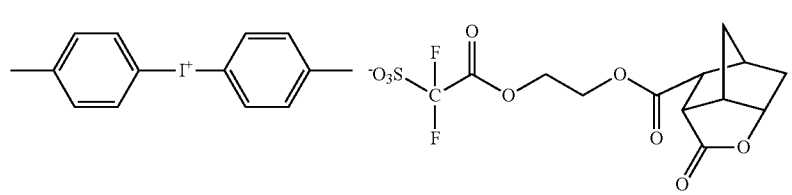
(I-54)
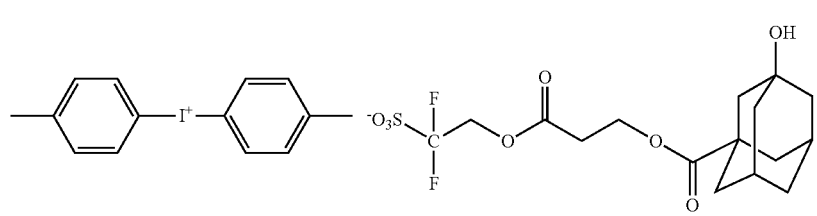
(I-55)

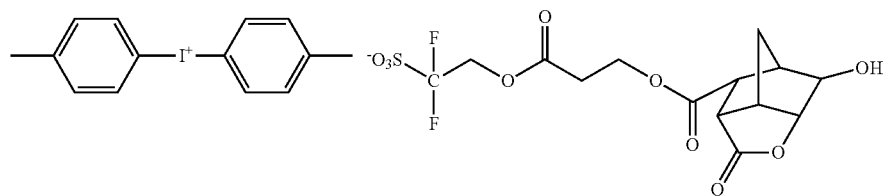
(I-56)
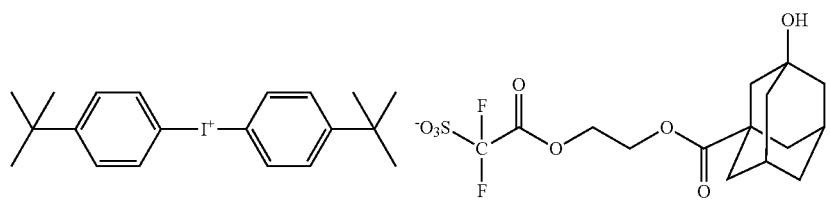
(I-57)
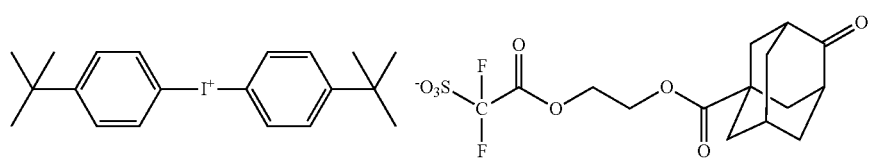
(I-58)
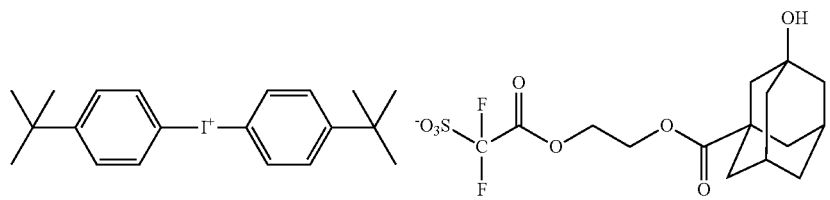
(I-59)
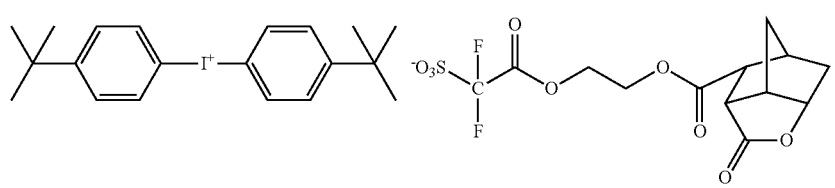
(I-60)
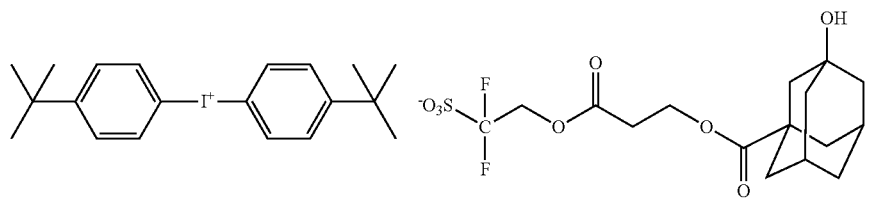
(I-61)
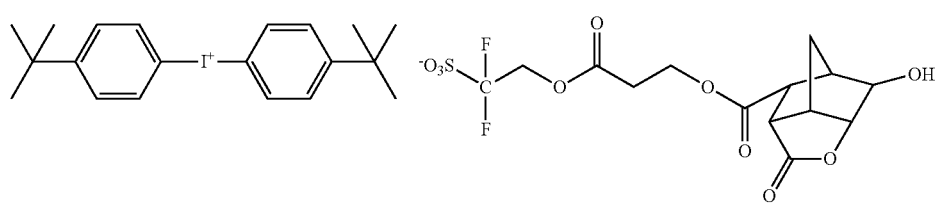
(I-62)

The salt represented by the formula (a1) can be produced by reacting a salt represented by the formula (1) with a salt represented by the formula (3) in an inert solvent such as acetonitrile, water, methanol, chloroform, methylene chloride and an aprotic solvent at 0 to 150° C., preferably 0 to 100° C., with stirring.

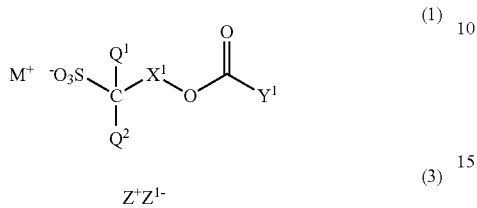

(1)

(3)

$Z^+Z^{1-}$ wherein $Q^1$, $Q^2$, $X^1$, $Y^1$ and $Z^+$ are the same as defined above, and $M^+$ represents $Li^+$, $Na^+$, $K^+$ or $Ag^+$, and $Z^{1-}$ represents $F^-$, $Cl^-$, $Br^-$, $I^-$, $BF_4^-$, $AsF_6^-$, $SbF_6^-$, $PF_6^-$ or $ClO_4^-$.

The amount of the salt of the formula (3) is usually 0.5 to 2 moles per 1 mole of the salt of the formula (1). The salt represented by the formula (a1) obtained can be taken out by recrystallization when it is in crystal form or by extraction by solvents and concentration when it is in oil form.

For example, the salt represented by the formula (1A) can be produced by reacting an alcohol compound represented by the formula (4A) with a carboxylic acid compound represented by the formula (5A).

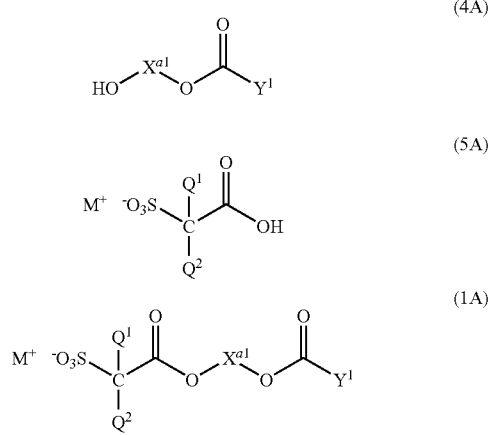

(4A)

(5A)

(1A)

wherein $Q^1$, $Q^2$, $X^{a1}$, $Y^1$ and $M^+$ are the same as defined above.

In the above-mentioned esterification reaction, the amount of the carboxylic acid compound of the formula (5A) is usually 0.2 to 3 moles, and preferably 0.5 to 2 moles per 1 mole of the alcohol compound of the formula (4A). The esterification reaction is usually in the presence of an acid catalyst, and the amount of the acid catalyst may be catalytic amount or the amount equivalent to solvent, and is usually 0.001 to 5 moles per 1 mole of the alcohol compound of the formula (4A).

The salt represented by the formula (1A) can be produced by reacting an alcohol compound represented by the formula (6A) with a carboxylic acid compound represented by the formula (7A), followed by conducting hydrolysis with MOH.

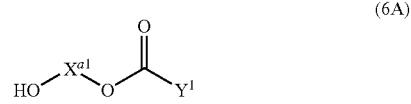

(6A)

(7A)

wherein $Q^1$, $Q^2$, $X^{a1}$ and $Y^1$ are the same as defined above.

The above-mentioned esterification reaction can generally be carried out by mixing materials in an aprotic solvent such as dichloroethane, toluene, ethylbenzene, monochlorobenzene, acetonitrile and N,N-dimethylformamide, at 20 to 200° C., preferably at 50 to 150° C. In the esterification reaction, an acid catalyst or a dehydrating agent is usually added, and examples of the acid catalyst include organic acids such as p-toluenesulfonic acid, and inorganic acids such as sulfuric acid. Examples of the dehydrating agent include 1,1'-carbonyldiimidazole, dicyclohexylcarbodiimide, 1-alkyl-2-halopyridinium salt, bis(2-oxo-3-oxazolizinyl)phosphinic chloride, 1-ethyl-3-(3-dimethylaminopropyl)carbodiimide hydrochloric acid salt, di-(2-pyridyl)carbonate, di-2-pyridylthiono carbonate, and 6-methyl-2-nitrobenzoic acid with 4-(dimethylamino)pyridine.

The esterification preferably is carried out with dehydration, for example, by Dean and Stark method as the reaction time tends to be shortened.

The photoresist composition of the present invention comprises a salt represented by the formula (a1) and a resin comprising a structural unit having an acid-labile group and being insoluble or poorly soluble in an aqueous alkali solution but becoming soluble in an aqueous alkali solution by the action of an acid. The photoresist composition can contain one or more acid generators other than the salt represented by the formula (a1).

Examples of the acid generators other than the salt represented by the formula (a1) include the followings.

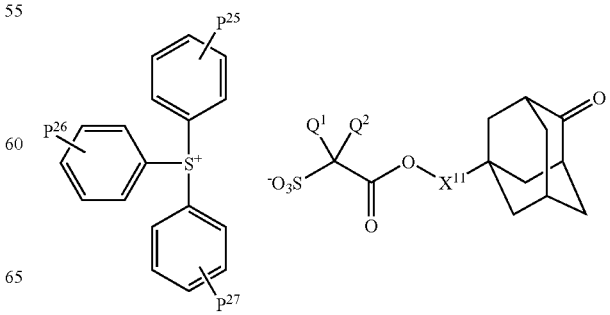

(Xa)

(Xb)
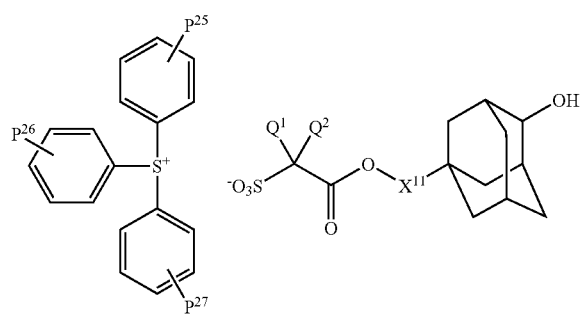

(Xc)
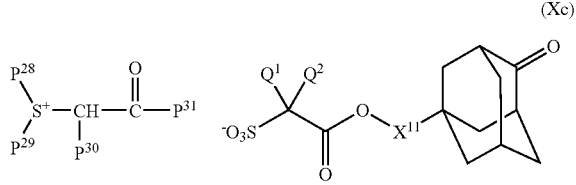

(Xd)
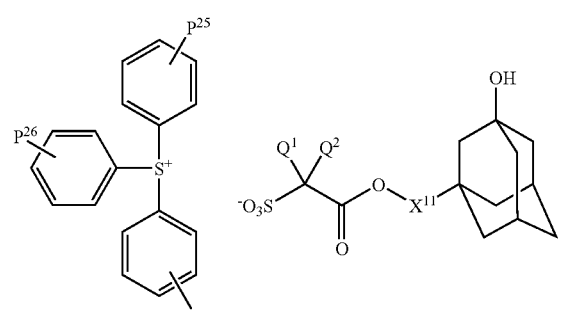

(Xe)
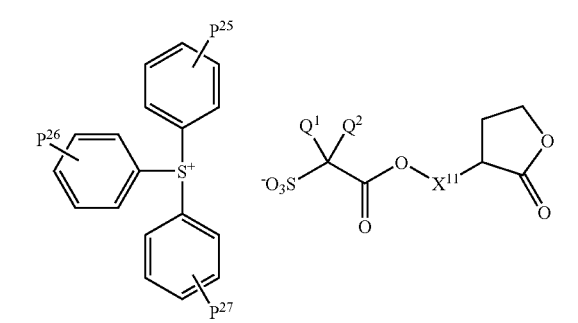

(Xf)
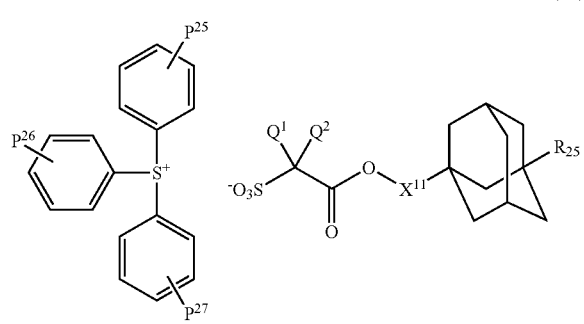

(Xg)
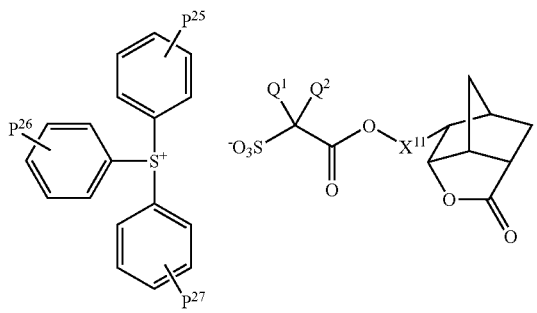

(Xh)
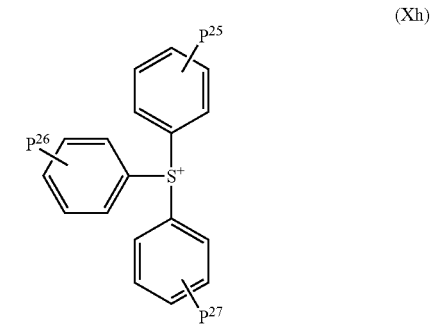

(Xi)

wherein $Q^1$ and $Q^2$ are the same as defined above, $P^{25}$, $P^{26}$ and $P^{27}$ independently each represent a hydrogen atom, a C1-C4 aliphatic hydrocarbon group or a C4-C36 alicyclic hydrocarbon group, $P^{28}$ and $P^{29}$ independently each represent a C1-C12 aliphatic hydrocarbon group or a C4-C36 alicyclic hydrocarbon group, or $P^{28}$ and $P^{29}$ are bonded each other to form a C2-C6 ring containing $S^+$, $P^{30}$ represents a C1-C12 aliphatic hydrocarbon group, a C4-C36 alicyclic hydrocarbon group or a C6-C20 aromatic group which may be substituted, or $P^{30}$ and $P^{31}$ are bonded each other to form a C3-C12 ring containing —CHCO—, and one or more —CH$_2$— in the ring can be replaced by —CO—, —O— or —S—, and $X^{11}$ represents a single bond or a methylene group, and $R^{25}$ represents a hydrogen atom, a hydroxyl group or a methyl group.

Examples of the ring formed by bonding $P^{28}$ and $P^{29}$ include a tetrahydrothiophenium group. Examples of the ring formed by bonding $P^{30}$ and $P^{31}$ include the above-mentioned groups represented by the formulae (W13) to (W15).

Preferable examples of the acid generators other than the salt represented by the formula (a1) include the followings.

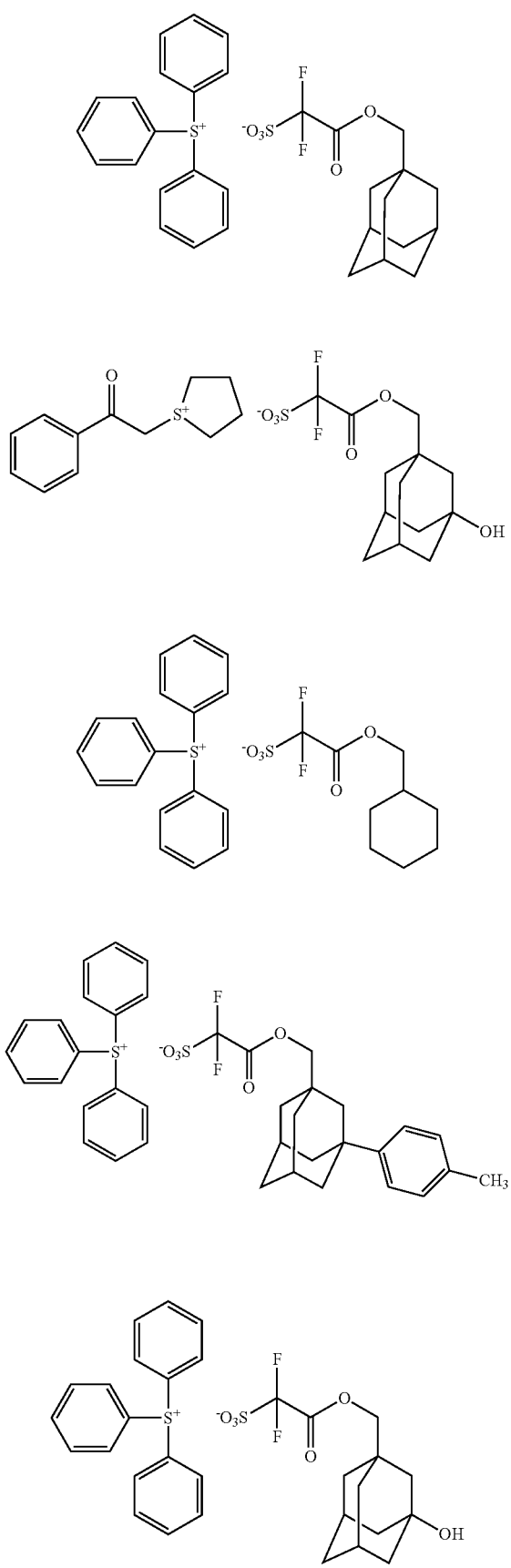
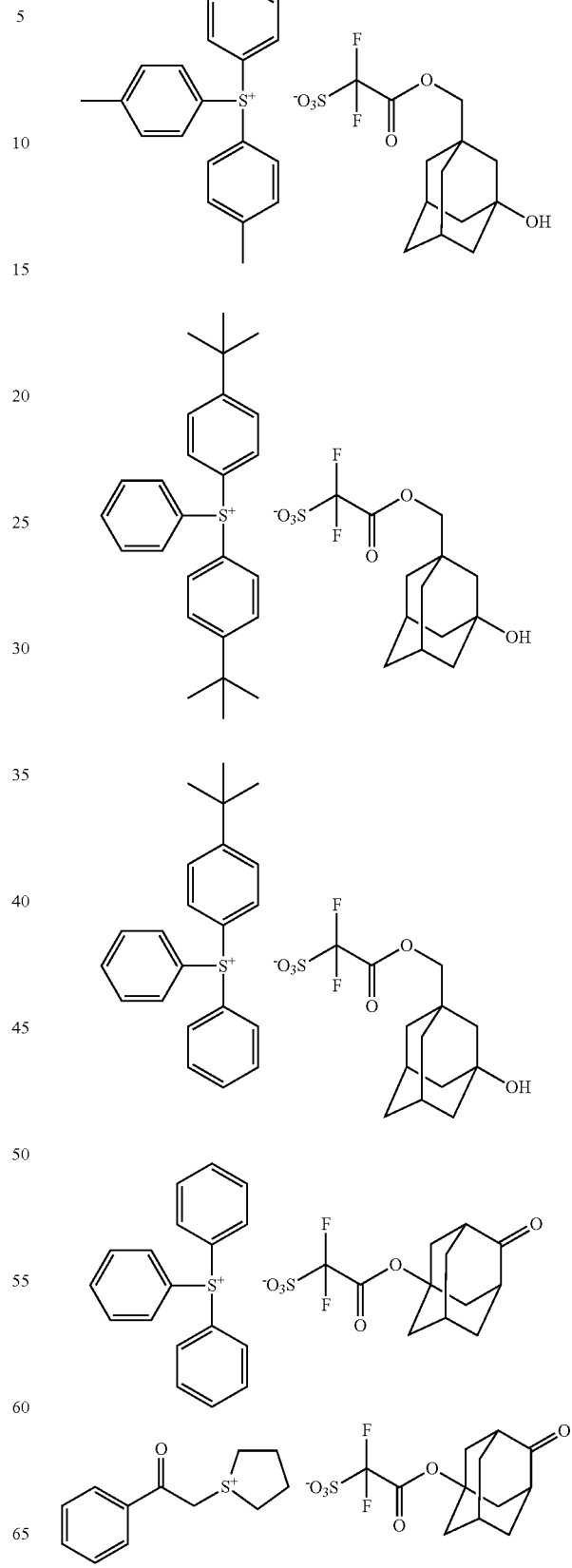

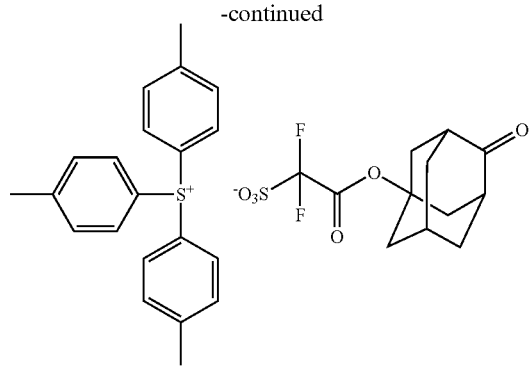
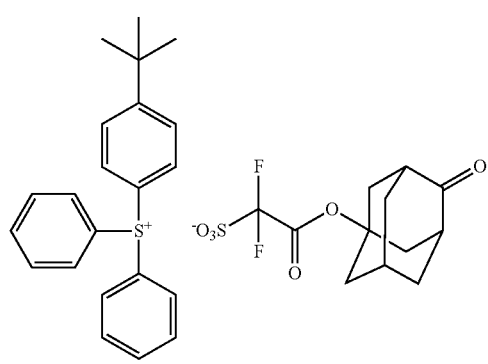
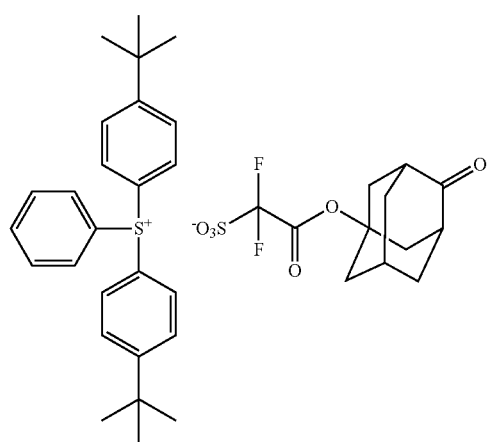
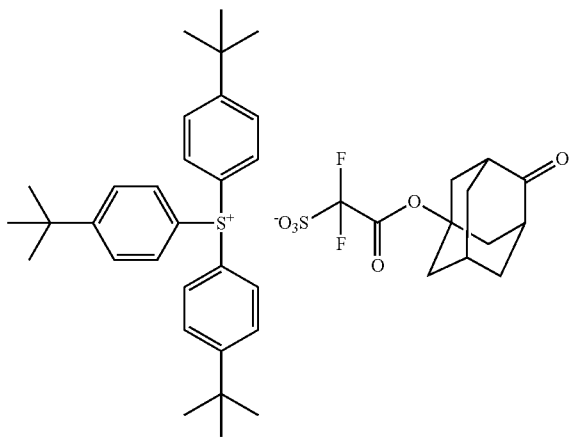
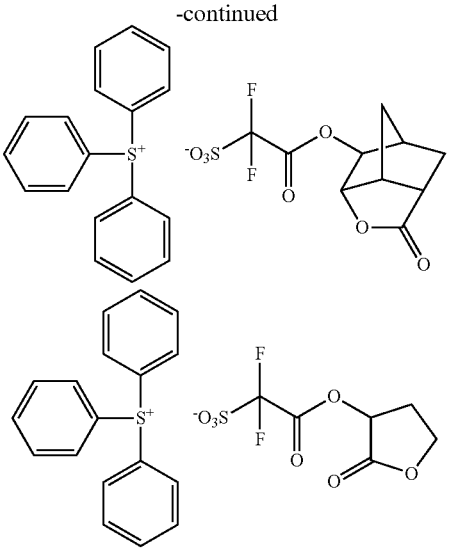
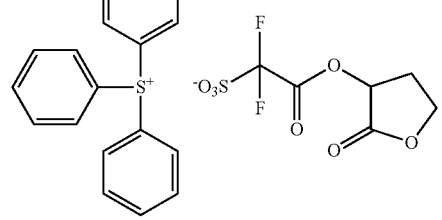

In this specification, "an acid-labile group" means a group capable of being eliminated by the action of an acid.

Examples of the acid-labile group include a group represented by the formula (10):

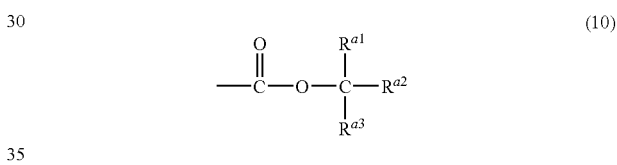

wherein $R^{a1}$, $R^{a2}$ and $R^{a3}$ independently each represent a C1-C8 aliphatic hydrocarbon group or a C3-C20 alicyclic hydrocarbon group, or $R^{a1}$ and $R^{a2}$ are bonded each other to form a C3-C20 ring.

Examples of the C1-C8 aliphatic hydrocarbon group include a C1-C8 alkyl group such as a methyl group, an ethyl group, a propyl group, an isopropyl group, a butyl group, a pentyl group, a hexyl group, a heptyl group and an octyl group. The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methyl norbornyl group, and the followings:

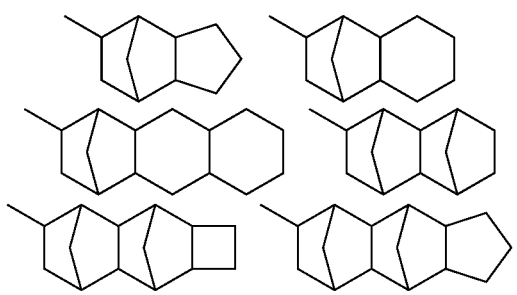

-continued

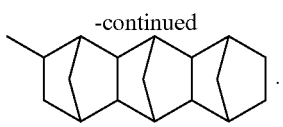

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

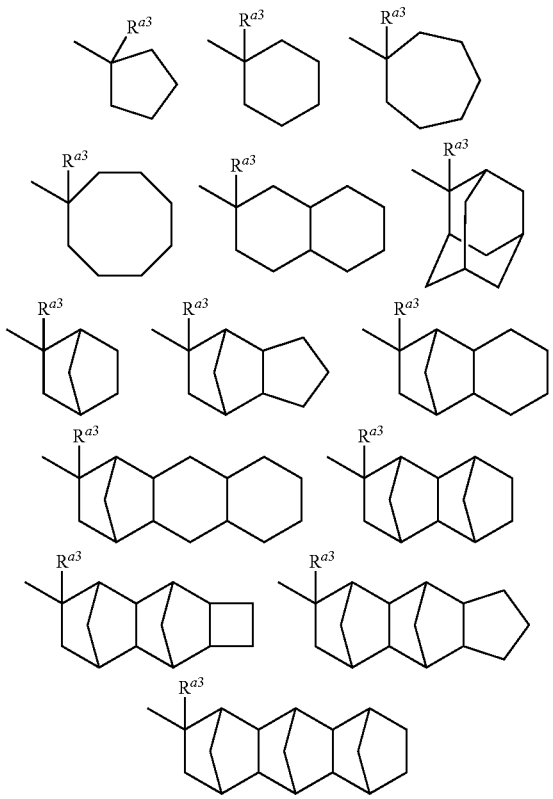

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The structural unit having an acid-labile group is derived from a monomer having an acid-labile group in its side chain and a carbon-carbon double bond, and an acrylate monomer having an acid-labile group in its side chain or a methacrylate monomer having an acid-labile group in its side chain is preferable.

Preferable examples of the monomer include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkyl methacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate. Particularly when the 2-alkyl-2-adamantyl acrylate or the 2-alkyl-2-adamantyl methacrylate is used as the monomer for the resin component in the photoresist composition, a photoresist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the photoresist composition, a photoresist composition having excellent sensitivity and heat resistance tends to be obtained.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

Two or more kinds of monomers having a group or groups dissociated by the action of the acid may be used together, if necessary.

The content of the structural unit having an acid-labile group in the resin is usually 10 to 80% by mole based on total molar of all the structural units of the resin.

The resin preferably contains one or more structural units having one or more highly polar substituents. Examples of the structural unit having one or more highly polar substituents include a structural unit having a hydrocarbon group having at least one selected from the group consisting of a hydroxyl group, a cyano group, a nitro group and an amino group and a structural unit having a hydrocarbon group having one or more —CO—O—, —CO—, —O—, —SO$_2$— or —S—. A structural unit having a saturated cyclic hydrocarbon group having a cyano group or a hydroxyl group, a structural unit having a saturated cyclic hydrocarbon group in which one or more —CH$_2$— replaced by —O— or —CO—, and a structural unit having a lactone structure in its side chain are preferable, and a structural unit having a bridged hydrocarbon group having one or more hydroxyl groups, and a structural unit having a bridged hydrocarbon group having —CO—O— or —CO— are more preferable. Examples thereof include a structural unit derived from 2-norbornene having one or more hydroxyl groups, a structural unit derived from acrylonitrile or methacrylonitrile, a structural unit derived from hydroxyl-containing adamantyl acrylate or hydroxyl-containing adamantyl methacrylate, a structural unit derived from styrene monomer such as p-hydroxystyrene and m-hydroxystyrene, a structural unit derived from a structural unit derived from 1-adamantyl acrylate or 1-adamantyl methacrylate, and a structural unit derived from acryloyloxy-γ-butyrolactone or methacryloyloxy-γ-butyrolactone having a lactone ring which may have an alkyl group.

Specific examples of the structural unit derived from hydroxyl-containing adamantyl acrylate or hydroxyl-containing adamantyl methacrylate include a structural unit derived from 3-hydroxy-1-adamantyl acrylate; a structural unit derived from 3-hydroxy-1-adamantyl methacrylate; a structural unit derived from 3,5-dihydroxy-1-adamantyl acrylate; and a structural unit derived from 3,5-dihydroxy-1-adamantyl methacrylate.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

When the resin has a structural unit derived from hydroxyl-containing adamantyl acrylate or hydroxyl-containing adamantyl methacrylate, the content thereof is preferably 5 to 50% by mole based on 100% by mole of all the structural units of the resin.

Examples of the structural unit derived from a monomer having a lactone ring which may have an alkyl group include a structural unit derived from acryloyloxy-γ-butyrolactone, a structural unit derived from methacryloyloxy-γ-butyrolactone and structural units represented by the formulae (a) and (b):

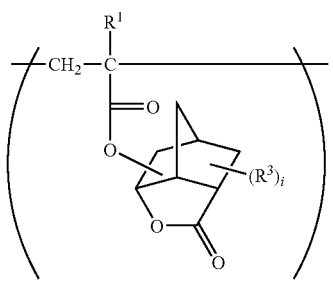

(a)

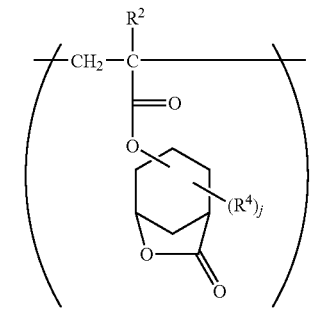

(b)

wherein $R^1$ and $R^2$ independently each represents a hydrogen atom or a methyl group, $R^3$ and $R^4$ are independently in each occurrence a hydrogen atom, a methyl group, a trifluoromethyl group or a halogen atom, and i and j independently each represents an integer of 1 to 3.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers giving structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

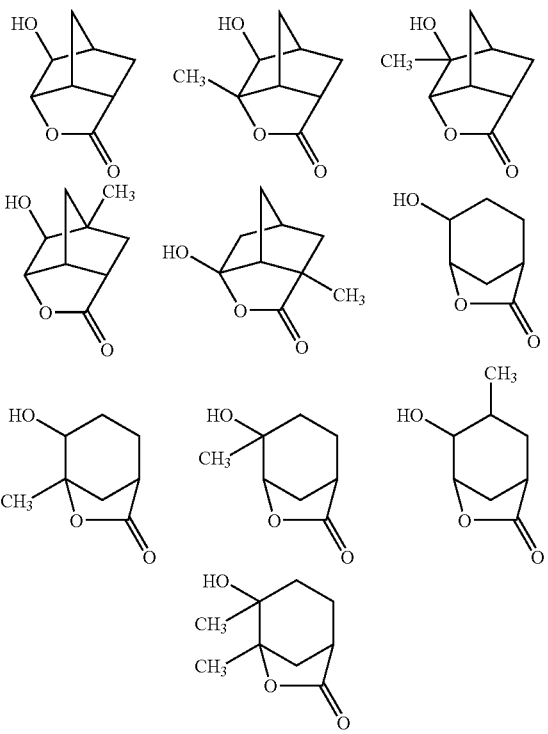

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

When the resin has a structural unit derived from a monomer having a lactone ring which may have an alkyl group, the content thereof is preferably 5 to 50% by mole based on 100% by mole of all the structural units of the resin.

Among them, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (a) and the structural unit represented by the formula (b) are preferable, because a photoresist composition having good resolution and adhesiveness of photoresist to a substrate tends to be obtained.

When the exposing is conducted using KrF excimer laser, the resin preferably has a structural unit derived from a styrene monomer such as p-hydroxystyrene and m-hydroxystyrene, and the content thereof is preferably 5 to 90% by mole based on 100% by mole of all the structural units of the resin.

The resin can contain a structural unit or units derived from a compound having one or more fluorine atoms. Examples of the structural unit derived from a compound having one or more fluorine atoms include the following structural unit represented by the formula (b1):

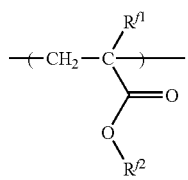

wherein $R^{f1}$ represents a methyl group or a trifluoromethyl group, and $R^{f2}$ represents a C1-C30 hydrocarbon group having one or more fluorine atoms, and one or more methylene groups in the C1-C30 hydrocarbon group can be replaced by —O— or —S—, and one or more hydrogen atoms in the C1-C30 hydrocarbon group can be replaced by a hydroxyl group.

Examples of the monomer giving the structural unit derived from a compound having one or more fluorine atoms include the followings.

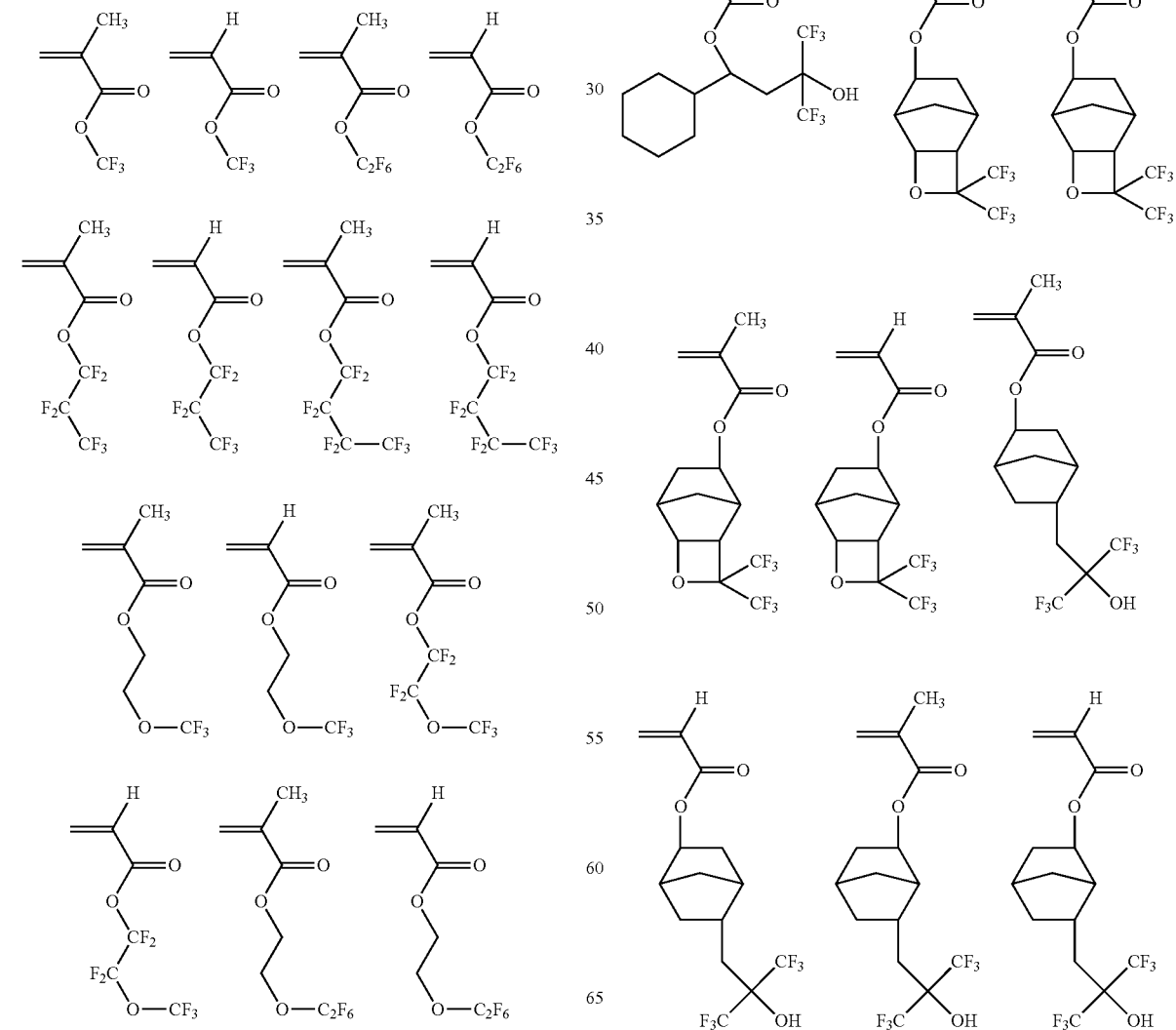

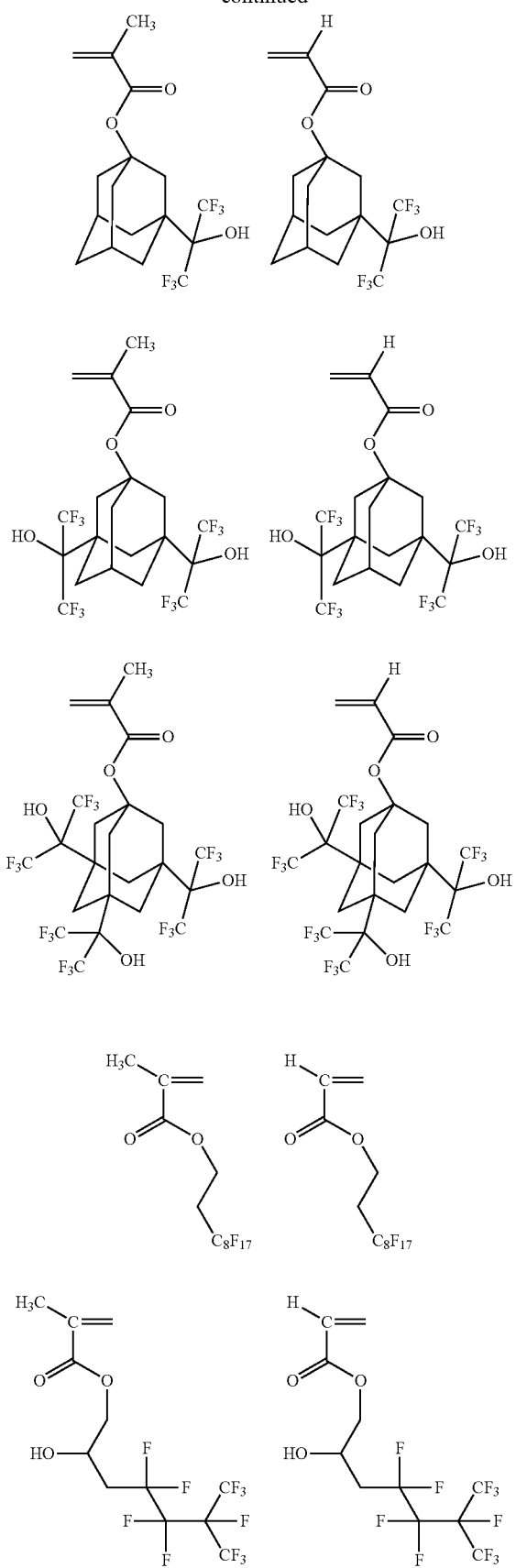
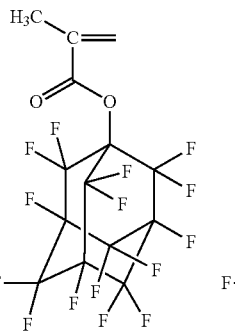
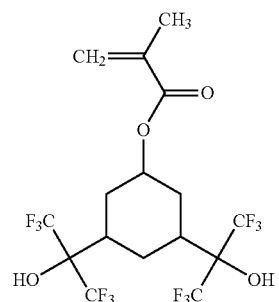
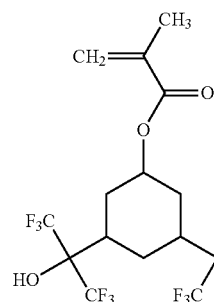

When the resin contains the structural unit derived from a compound having one or more fluorine atoms, the content thereof is preferably 5 to 90% by mole based on 100% by mole of all the structural units of the resin.

The resin can contain the other structural unit or units. Examples thereof include a structural unit derived from acrylic acid or methacrylic acid, a structural unit derived from an alicyclic compound having an olefinic double bond such as a structural unit represented by the formula (c):

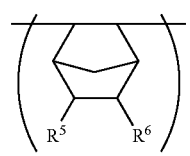

(c)

wherein $R^5$ and $R^6$ each independently represents a hydrogen atom, a C1-C3 alkyl group, a carboxyl group, a cyano group or a —COOU group in which U represents an alcohol residue, or $R^5$ and $R^6$ can be bonded together to form a carboxylic anhydride residue represented by —C(=O)OC(=O)—, a structural unit derived from an aliphatic unsaturated dicarboxylic anhydride such as a structural unit represented by the formula (d):

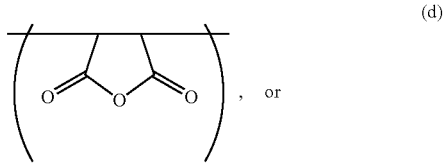

(d)

a structural unit represented by the formula (e):

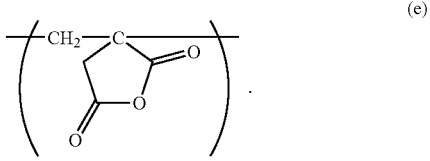

In $R^5$ and $R^6$, examples of the C1-C3 alkyl group include a methyl group, an ethyl group, a propyl group and an isopropyl group. The —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer giving the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin can be obtained by conducting polymerization reaction of a monomer or monomers having the acid-labile group and an olefinic double bond. The polymerization reaction is usually carried out in the presence of a radical initiator. This polymerization reaction can be conducted according to known methods.

The resin usually has 10,000 or more of the weight-average molecular weight, preferably 10,500 or more of the weight-average molecular weight, more preferably 11,000 or more of the weight-average molecular weight, much more preferably 11,500 or more of the weight-average molecular weight, and especially preferably 12,000 or more of the weight-average molecular weight. When the weight-average molecular weight of the resin is too large, defect of the photoresist film tends to generate, and therefore, the resin preferably has 40,000 or less of the weight-average molecular weight, more preferably 39,000 or less of the weight-average molecular weight, much more preferably 38,000 or less of the weight-average molecular weight, and especially preferably 37,000 or less of the weight-average molecular weight. The weight-average molecular weight can be measured with gel permeation chromatography.

The present resist composition preferably includes 80 to 99.9% by weight of the resin component and 0.1 to 20% by weight of the acid generator component based on sum of the resin component and the acid generator component. Herein, "acid generator component" means the salt represented by the formula (a1) and the other acid generator(s) contained in the photoresist composition.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

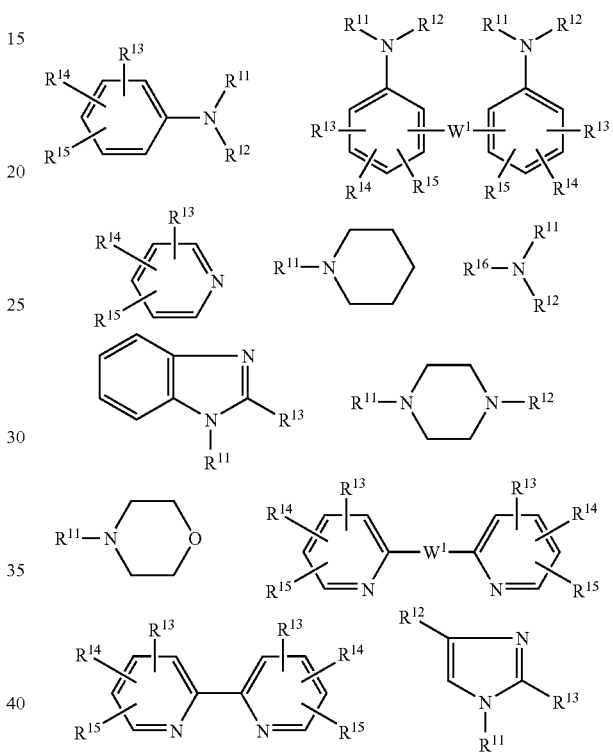

wherein $R^{11}$ and $R^{12}$ independently represent a hydrogen atom, a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, a C1-C6 alkyl group, a C5-C10 cycloalkyl group, a C6-C10 aryl group or a C1-C6 alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, a C1-C6 alkyl group, a C5-C10 cycloalkyl group, a C6-C10 aryl group, a C1-C6 alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents a C1-C6 alkyl group or a C5-C10 cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, an C2-C6 alkylene group, and a quaternary ammonium hydroxide represented by the following formula:

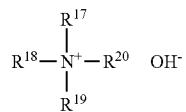

wherein $R^{17}$, $R^{18}$, $R^{19}$ and $R^{20}$ independently represent a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

Examples of the amino group which may be substituted with the C1-C4 alkyl group include an amino group, a methylamino group, an ethylamino group, a butylamino group, a dimethylamino group and a diethylamino group. Examples of the C1-C6 alkoxy group which may be substituted with the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the C1-C6 alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, a propyl group, an isopropyl group, a butyl group, a tert-butyl group, a pentyl group, a hexyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the C5-C10 cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

Specific examples of the C6-C10 aryl group which may be substituted with at least one group selected from the group consisting of a hydroxyl group, an amino group which may be substituted with a C1-C4 alkyl group or a C1-C6 alkoxy group include a phenyl group and a naphthyl group.

Specific examples of the C1-C6 alkoxy group include a methoxy group, an ethoxy group, a propoxy group, an isopropoxy group, a butoxy group, a tert-butoxy group, a pentyloxy group and a hexyloxy group.

Specific examples of the C2-C6 alkylene group include an ethylene group, a trimethylene group and a tetramethylene group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern. The alkaline developer used may be any one of various alkaline aqueous solution used in the art. Generally, an aqueous solution of tetramethylammonium hydroxide or (2-hydroxyethyl) trimethylammonium hydroxide (commonly known as "choline") is often used.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran] using polystyrene as a standard reference material. Structures of compounds were determined by NMR (EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1-1

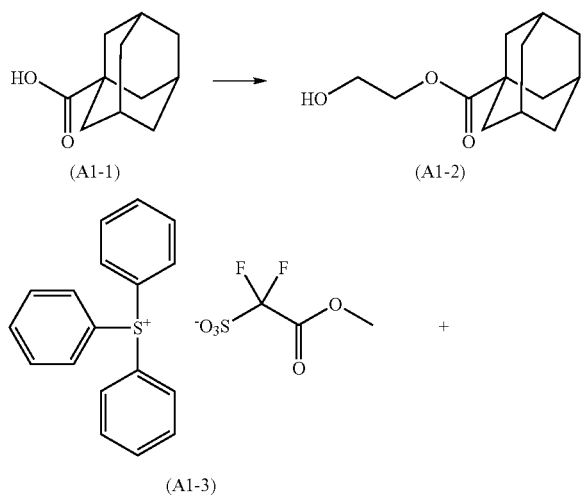

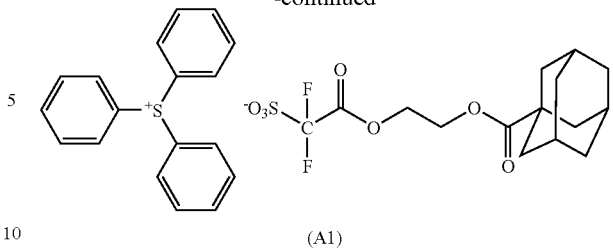

A mixture of 10.00 parts of a compound represented by the formula (A1-1), 34.44 parts of ethylene glycol and 0.27 part of sulfuric acid was stirred at 23° C. for 30 minutes. The obtained mixture was dehydrated for 1 hour with heating at 105° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 12.38 parts of a compound represented by the formula (A1-2).

A mixture of 4.98 parts of a salt represented by the formula (A1-3), 10.00 parts of chloroform, 3.02 parts of the compound represented by the formula (A1-2), which was obtained above, and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether and the supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 3.82 parts of a salt represented by the above-mentioned formula (A1) in the form of oil. This is called as acid generator A1.

MS (ESI(+) Spectrum): M⁺ 263.1
MS (ESI(−) Spectrum): M⁻ 381.1
¹H-NMR (dimethylsulfoxide-d₆, Internal Standard: tetramethylsilane): δ (ppm) 1.52-2.05 (m, 15H), 4.15-4.25 (m, 2H), 4.35-4.45 (m, 2H), 7.70-7.90 (m, 15H)

Example 1-2

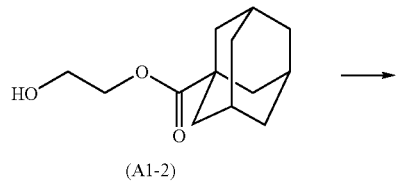

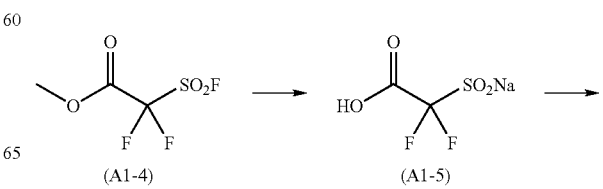

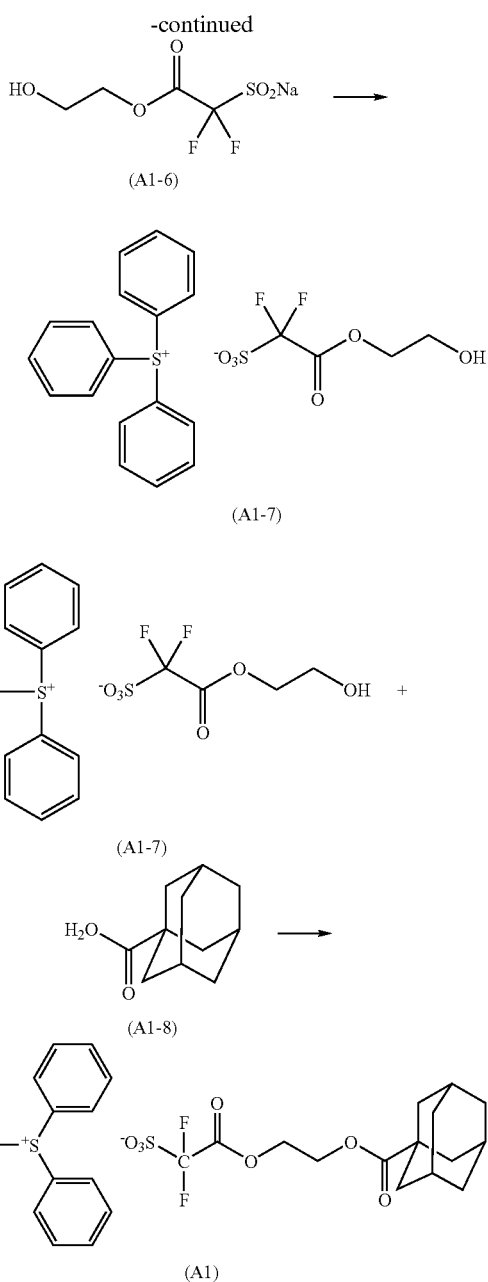

A mixture of 100 parts of a compound represented by the formula (A1-4) and 250 parts of ion-exchanged water was stirred at 23° C. for 30 minutes. To the obtained mixture, 230 parts of 30% aqueous sodium hydroxide solution was added dropwise in an ice bath. The resultant mixture was heated and refluxed at 100° C. for 3 hours. After cooling, the mixture was mixed with 88 parts of concentrated hydrochloric acid and the solution obtained was concentrated to obtain 165.0 parts of a compound represented by the formula (A1-5) (containing inorganic salt, purity: 62.5%).

A mixture of 8.00 parts of a compound represented by the formula (A1-5) (purity: 62.5%), 1.57 parts of ethylene glycol and 60 parts of dichloroethane was stirred at 23° C. for 30 minutes. To the obtained mixture, 1.24 parts of sulfuric acid was added and the resultant mixture was refluxed for 4 hours. The obtained mixture was concentrated and the obtained residue was mixed with 100 parts of ethyl acetate. The obtained mixture was stirred at 23° C. for 30 minutes followed by filtration. The obtained filtrate was concentrated to obtain 9.25 parts of a salt represented by the formula (A1-6).

A mixture of 9.25 parts of the salt represented by the formula (A1-6) and 92.50 parts of acetonitrile was stirred at 23° C. for 30 minutes. To the obtained solution, a solution prepared by dissolving 11.40 parts of triphenylsulfonium chloride in 60 parts of ion-exchanged water was added. The resultant mixture was stirred for 15 hours. The obtained mixture was concentrated. To the obtained residue, 100 parts of chloroform was added and the obtained mixture was separated to an organic layer and an aqueous layer. The obtained organic layer was washed with 100 parts of ion-exchanged water and concentrated. The obtained residue was mixed with 50 parts of methyl tert-butyl ether and the resultant mixture was stirred at 23° C. for 30 minutes followed by filtration. The obtained solid was mixed with 50 parts of ethyl acetate and the resultant mixture was stirred at 23° C. for 30 minutes followed by filtration to obtain 5.54 parts of a salt represented by the formula (A1-7) in the form of white solid.

A mixture of 4.83 parts of a salt represented by the formula (A1-7), 1.80 parts of a compound represented by the formula (A1-8) and 25 parts of monochlorobenzene was stirred at 23° C. for 30 minutes. To the obtained mixture, 0.98 part of sulfuric acid and 14.00 parts of molecular sieves 3A, available from Wako Pure Chemical Industries, Ltd. were added, and the resultant mixture was stirred at 135° C. for 8 hours. The obtained mixture was cooled and then, concentrated. The obtained residue was mixed with 40.00 parts of chloroform and the resultant mixture was stirred at 23° C. for 30 minutes. The mixture was washed with 15.00 parts of ion-exchanged water and the obtained organic layer was washed with ion-exchanged water and then, concentrated. The obtained residue was mixed with 10 parts of ethyl acetate, and then, the supernatant solution was removed. The obtained residue was mixed with 10 parts of methyl tert-butyl ether and the supernatant solution was removed. The obtained residue was concentrated followed by mixing with 10 parts of ethyl acetate. The supernatant solution was removed, and the obtained residue was mixed with 10 parts of methyl tert-butyl ether and the supernatant solution was removed. The obtained residue was dissolved in chloroform, and the obtained solution was concentrated to obtain 2.44 parts of a salt represented by the above-mentioned formula (A1) in the form of oil. This is called as acid generator A1.

MS (ESI(+) Spectrum): M$^+$ 263.1

MS (ESI(−) Spectrum): M$^−$ 381.1

$^1$H-NMR (dimethylsulfoxide-d$_6$, Internal Standard: tetramethylsilane): δ (ppm) 1.52-2.05 (m, 15H), 4.15-4.25 (m, 2H), 4.35-4.45 (m, 2H), 7.70-7.90 (m, 15H)

Example 2-1

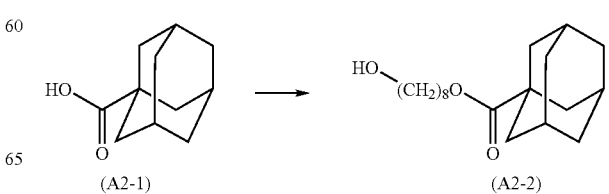

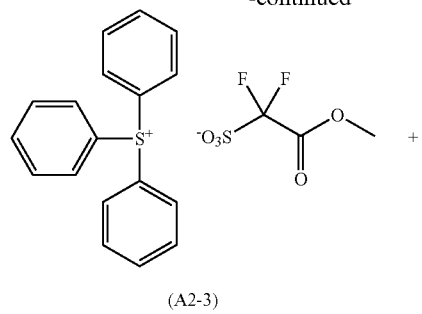

(A2-3)

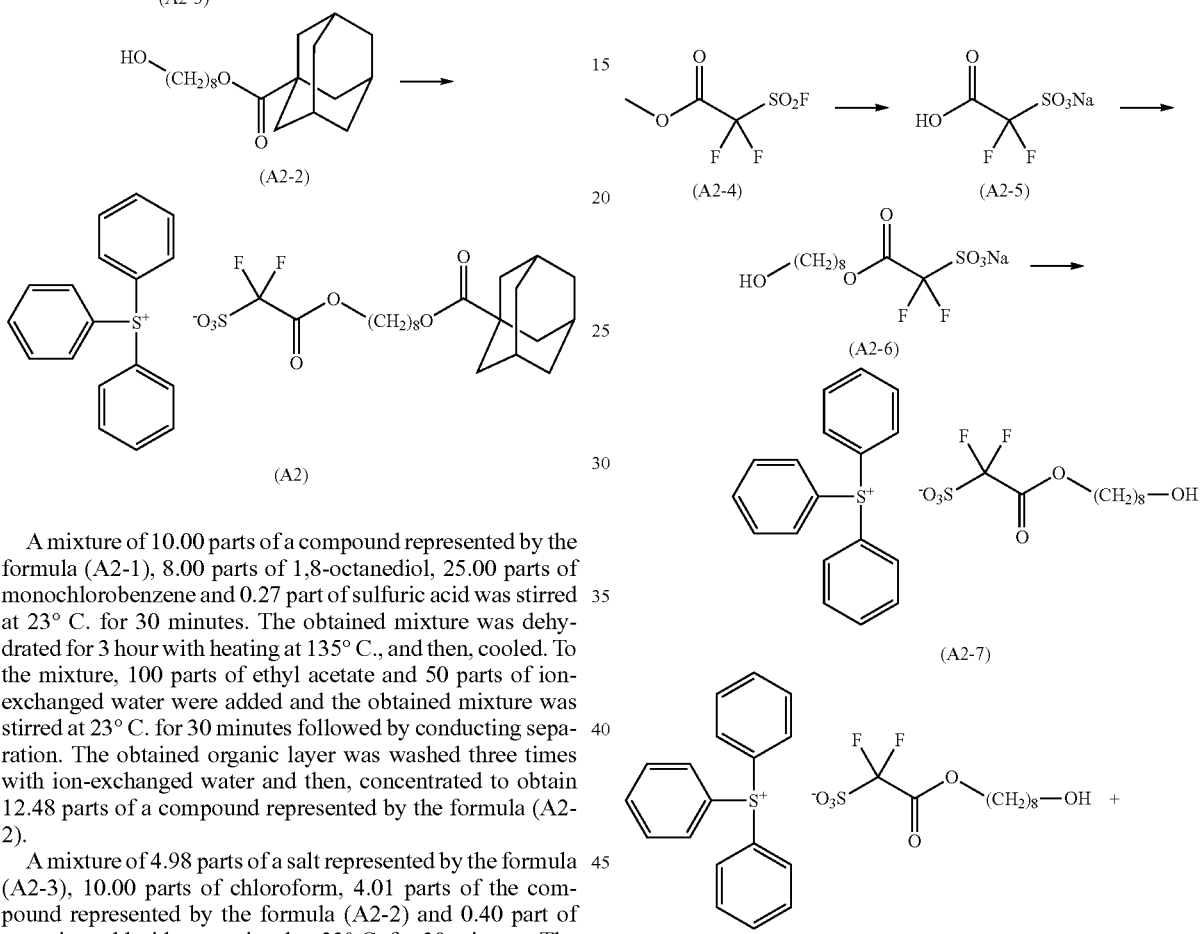

A mixture of 10.00 parts of a compound represented by the formula (A2-1), 8.00 parts of 1,8-octanediol, 25.00 parts of monochlorobenzene and 0.27 part of sulfuric acid was stirred at 23° C. for 30 minutes. The obtained mixture was dehydrated for 3 hour with heating at 135° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 12.48 parts of a compound represented by the formula (A2-2).

A mixture of 4.98 parts of a salt represented by the formula (A2-3), 10.00 parts of chloroform, 4.01 parts of the compound represented by the formula (A2-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether and the supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 5.21 parts of a salt represented by the above-mentioned formula (A2) in the form of oil. This is called as acid generator A2.

MS (ESI(+) Spectrum): $M^+$ 263.1

MS (ESI(−) Spectrum): $M^-$ 465.2

$^1$H-NMR (dimethylsulfoxide-$d_6$, Internal Standard: tetramethylsilane): δ (ppm) 1.26-1.42 (m, 8H), 1.52-2.15 (m, 19H), 4.15-4.45 (m, 4H), 7.70-7.90 (m, 15H)

Example 2-2

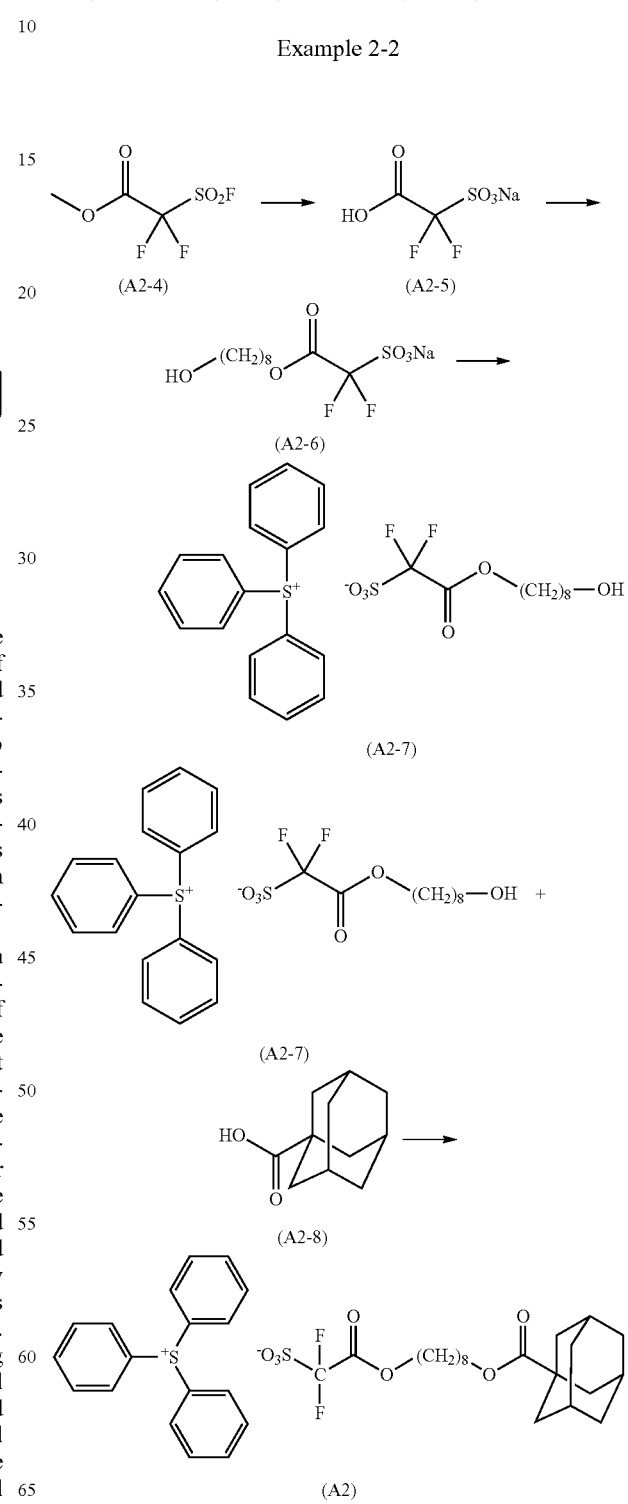

A mixture of 500 parts of a compound represented by the formula (A2-4) and 750 parts of ion-exchanged water was stirred at 23° C. for 30 minutes. To the obtained mixture, 424 parts of 30% aqueous sodium hydroxide solution was added dropwise in an ice bath. The resultant mixture was heated and refluxed at 100° C. for 2.5 hours. After cooling, the mixture was mixed with 440 parts of concentrated hydrochloric acid and the solution obtained was concentrated to obtain 802.82 parts of a compound represented by the formula (A2-5) (containing inorganic salt, purity: 64.2%).

A mixture of 5.0 parts of a compound represented by the formula (A2-5) (purity: 64.2%), 2.32 parts of 1,8-octanediol and 60 parts of dichloroethane was stirred at 23° C. for 30 minutes. To the obtained mixture, 3.02 parts of p-toluenesulfonic acid was added and the resultant mixture was refluxed for 4.5 hours. The obtained mixture was concentrated and the obtained residue was mixed with 100 parts of methyl tert-butyl ether. The obtained mixture was stirred at 23° C. for 30 minutes followed by filtration. The obtained solid was mixed with 100 parts of acetonitrile. The obtained mixture was stirred at 23° C. for 30 minutes followed by filtration. The obtained filtrate was concentrated to obtain 2.82 parts of a salt represented by the formula (A2-6) (containing a diester compound, purity: 41.2%).

A mixture of 2.82 parts of the salt represented by the formula (A2-6) and 28.2 parts of acetonitrile was stirred at 23° C. for 30 minutes. To the obtained solution, a solution prepared by dissolving 3.19 parts of triphenylsulfonium chloride in 31.9 parts of ion-exchanged water was added. The resultant mixture was stirred at 23° C. for 15 hours. The obtained mixture was concentrated. To the obtained residue, 50 parts of chloroform was added and the obtained mixture was separated to an organic layer and an aqueous layer. The obtained organic layer was washed with 30 parts of ion-exchanged water and concentrated. The obtained residue was mixed with 30 parts of methyl tert-butyl ether and the resultant mixture was stirred at 23° C. for 30 minutes followed by filtration. The obtained solid was mixed with 50 parts of ethyl acetate and the resultant mixture was stirred at 23° C. for 30 minutes followed by filtration. The obtained filtrate was concentrated to obtain 0.73 part of a salt represented by the formula (A2-7) in the form of colorless liquid.

A mixture of 5.67 parts of a salt represented by the formula (A2-7), 1.80 parts of a compound represented by the formula (A2-8) and 30.00 parts of monochlorobenzene was stirred at 23° C. for 30 minutes. To the obtained mixture, 0.98 part of sulfuric acid and 15.00 parts of molecular sieves 3A, available from Wako Pure Chemical Industries, Ltd., were added, and the resultant mixture was stirred at 135° C. for 4 hours. The obtained mixture was cooled and then, concentrated. The obtained residue was mixed with 30.00 parts of chloroform and the resultant mixture was stirred at 23° C. for 30 minutes. The mixture was washed with 15.00 parts of ion-exchanged water and the obtained organic layer was washed with ion-exchanged water and then, concentrated. The obtained residue was mixed with 20 parts of ethyl acetate, and then, the obtained mixture was stirred at 23° C. for 30 minutes. The mixture was filtrated to obtain 2.68 parts of a salt represented by the above-mentioned formula (A2) in the form of white solid. This is called as acid generator A2.

MS (ESI(+) Spectrum): M$^+$ 263.1

MS (ESI(−) Spectrum): M$^-$ 465.2

$^1$H-NMR (dimethylsulfoxide-d$_6$, Internal Standard: tetramethylsilane): δ (ppm) 1.26-1.42 (m, 8H), 1.52-2.15 (m, 19H), 4.15-4.45 (m, 4H), 7.70-7.90 (m, 15H)

Example 3

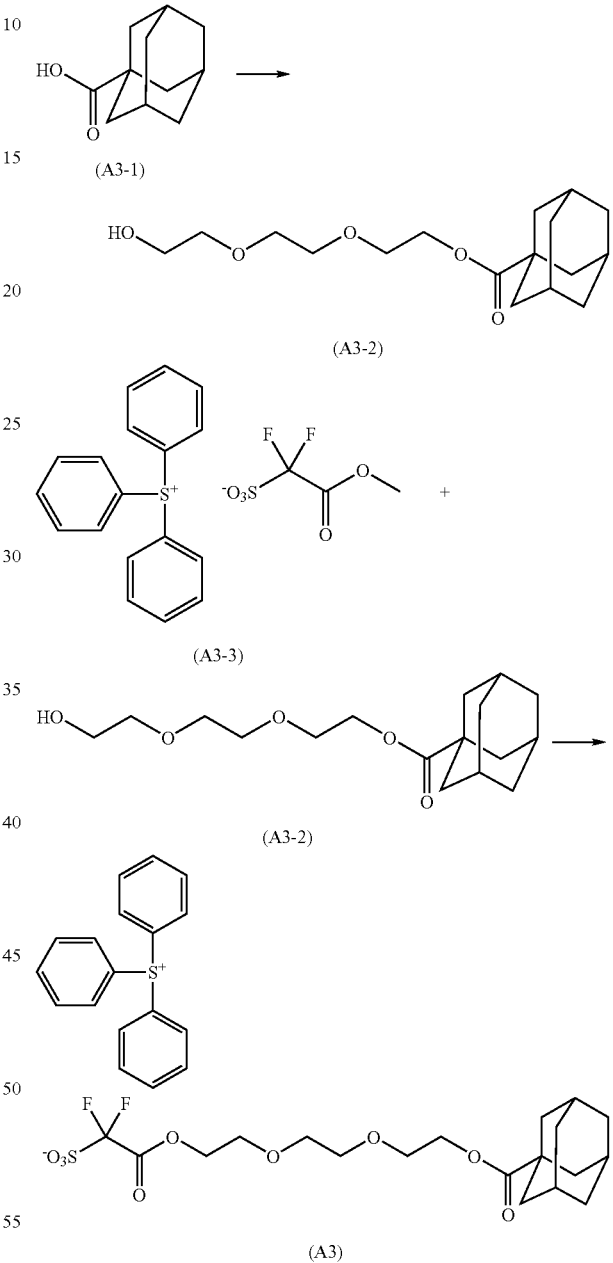

A mixture of 10.00 parts of a compound represented by the formula (A3-1), 24.78 parts of triethylene glycol, 45.00 parts of monochlorobenzene and 0.27 part of sulfuric acid was stirred at 23° C. for 30 minutes. The obtained mixture was dehydrated for 3 hour with heating at 135° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 12.86 parts of a compound represented by the formula (A3-2).

A mixture of 4.98 parts of a salt represented by the formula (A3-3), 10.00 parts of chloroform, 4.06 parts of the compound represented by the formula (A3-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 3.69 parts of a salt represented by the above-mentioned formula (A3) in the form of oil. This is called as acid generator A3.

MS (ESI(+) Spectrum): M⁺ 263.1

MS (ESI(−) Spectrum): M⁻ 469.1

$^1$H-NMR (dimethylsulfoxide-$d_6$, Internal Standard: tetramethylsilane): δ (ppm) 1.52-2.05 (m, 15H), 3.39-3.69 (m, 8H), 4.15-4.45 (m, 4H), 7.70-7.90 (m, 15H)

Example 4

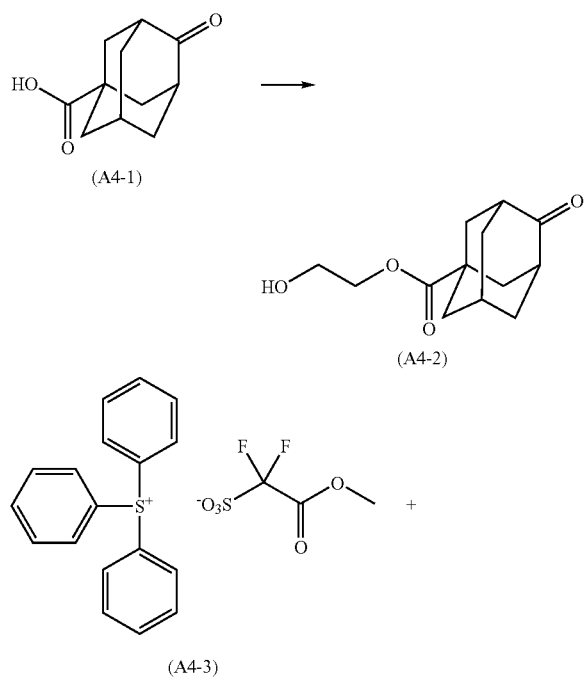

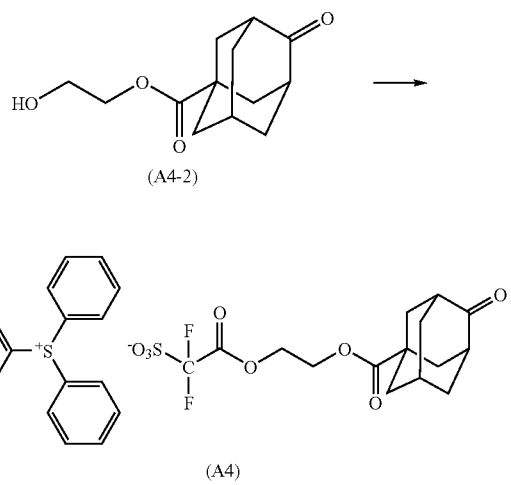

A mixture of 10.68 parts of a compound represented by the formula (A4-1), 34.44 parts of ethylene glycol and 0.27 part of sulfuric acid was stirred at 23° C. for 30 minutes. The obtained mixture was dehydrated for 1 hour with heating at 105° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 13.01 parts of a compound represented by the formula (A4-2).

A mixture of 4.98 parts of a salt represented by the formula (A4-3), 10.00 parts of chloroform, 3.10 parts of the compound represented by the formula (A4-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 5.88 parts of a salt represented by the above-mentioned formula (A4) in the form of oil. This is called as acid generator A4.

MS (ESI(+) Spectrum): M⁺ 263.1

MS (ESI(−) Spectrum): M⁻ 395.1

¹H-NMR (dimethylsulfoxide-d₆, Internal Standard: tetramethylsilane): δ (ppm) 1.60-2.15 (m, 11H), 2.25-2.30 (m, 2H), 4.15-4.45 (m, 4H), 7.70-7.90 (m, 15H)

Example 5

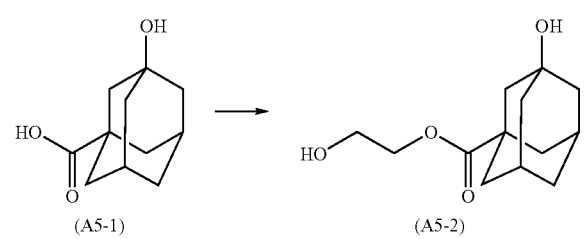

(A5-1)     (A5-2)

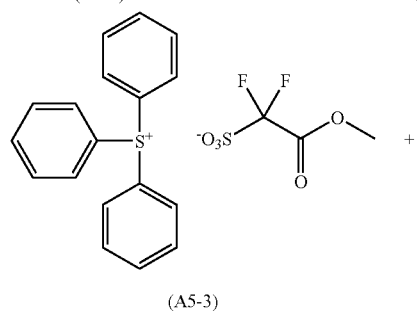

(A5-3)

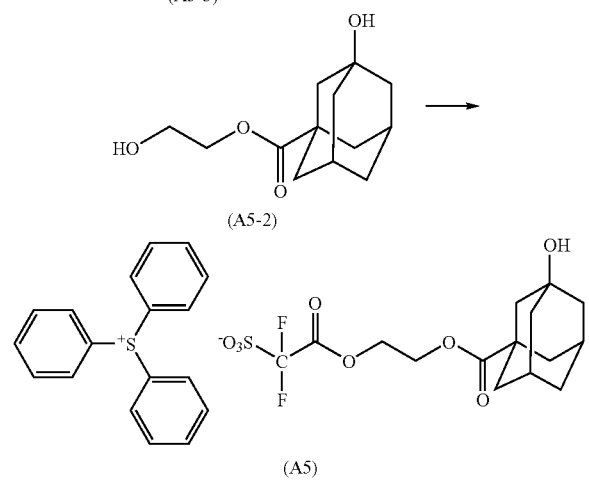

(A5-2)

(A5)

A mixture of 10.79 parts of a compound represented by the formula (A5-1), 34.44 parts of ethylene glycol and 0.27 part of sulfuric acid was stirred at 23° C. for 30 minutes. The obtained mixture was dehydrated for 1 hour with heating at 105° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 12.44 parts of a compound represented by the formula (A5-2).

A mixture of 4.98 parts of a salt represented by the formula (A5-3), 10.00 parts of chloroform, 3.12 parts of the compound represented by the formula (A5-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 4.99 parts of a salt represented by the above-mentioned formula (A5) in the form of oil. This is called as acid generator A5.

MS (ESI(+) Spectrum): M⁺ 263.1
MS (ESI(−) Spectrum): M⁻ 397.1
¹H-NMR (dimethylsulfoxide-d₆, Internal Standard: tetramethylsilane): δ (ppm) 1.60-2.20 (m, 14H), 4.15-4.45 (m, 5H), 7.70-7.90 (m, 15H)

Example 6

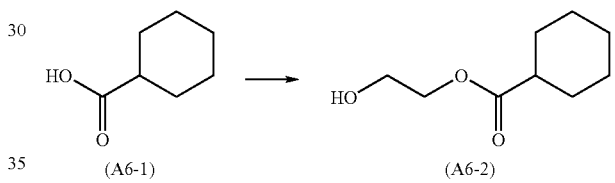

(A6-1)     (A6-2)

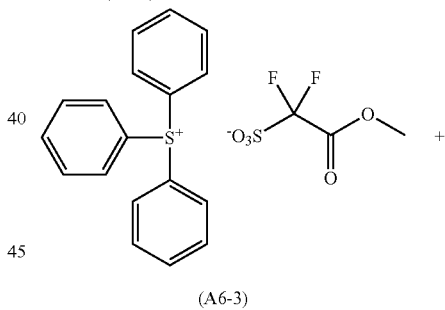

(A6-3)

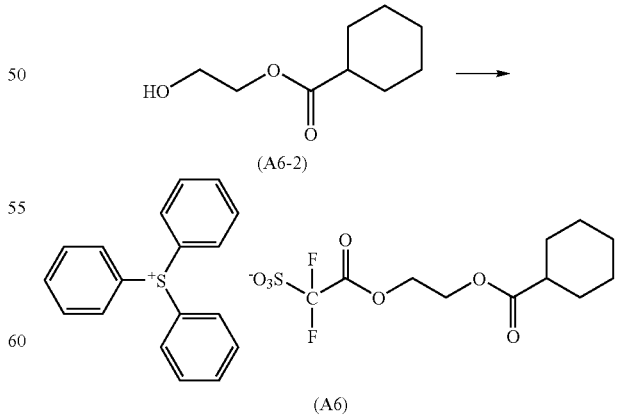

(A6-2)

(A6)

A mixture of 7.05 parts of a compound represented by the formula (A6-1), 34.44 parts of ethylene glycol and 0.27 part of sulfuric acid was stirred at 23° C. for 30 minutes. The obtained mixture was dehydrated for 1 hour with heating at 105° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 9.86 parts of a compound represented by the formula (A6-2).

A mixture of 4.98 parts of a salt represented by the formula (A6-3), 10.00 parts of chloroform, 2.24 parts of the compound represented by the formula (A6-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 3.12 parts of a salt represented by the above-mentioned formula (A6) in the form of oil. This is called as acid generator A6.

MS (ESI(+) Spectrum): M$^+$ 263.1
MS (ESI(−) Spectrum): M$^-$ 329.1

$^1$H-NMR (dimethylsulfoxide-d$_6$, Internal Standard: tetramethylsilane): δ (ppm) 1.12-2.16 (m, 10H), 2.28-2.40 (m, 1H), 4.15-4.45 (m, 4H), 7.70-7.90 (m, 15H)

Example 7

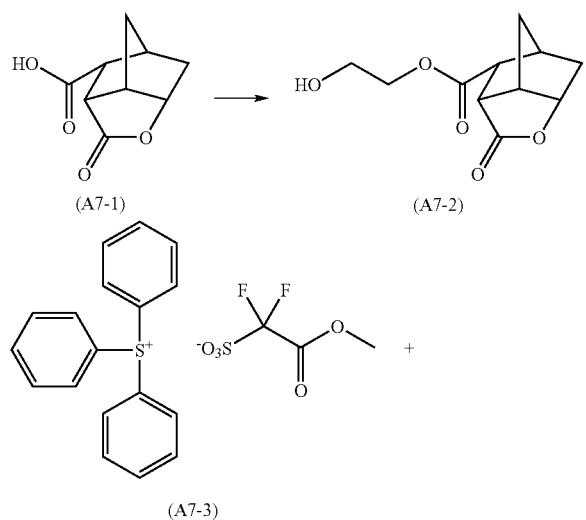

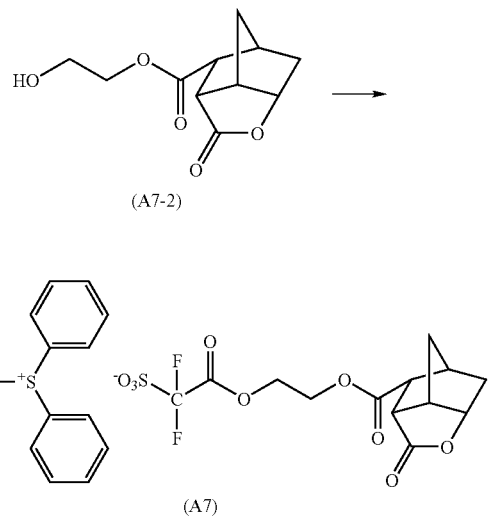

A mixture of 10.02 parts of a compound represented by the formula (A7-1), 34.44 parts of ethylene glycol and 0.27 part of sulfuric acid was stirred at 23° C. for 30 minutes. The obtained mixture was dehydrated for 1 hour with heating at 105° C., and then, cooled. To the mixture, 100 parts of ethyl acetate and 50 parts of ion-exchanged water were added and the obtained mixture was stirred at 23° C. for 30 minutes followed by conducting separation. The obtained organic layer was washed three times with ion-exchanged water and then, concentrated to obtain 9.86 parts of a compound represented by the formula (A7-2).

A mixture of 4.98 parts of a salt represented by the formula (A7-3), 10.00 parts of chloroform, 2.94 parts of the compound represented by the formula (A7-2) and 0.40 part of samarium chloride was stirred at 23° C. for 30 minutes. The obtained mixture was dehydrated for 20 hours with heating at 60° C., and then, cooled. To the mixture, 50 parts of chloroform and 30 parts of ion-exchanged water were added, and the obtained mixture was stirred at 23° C. for 30 minutes followed by conducting separation. The obtained organic layer was washed four times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 2.64 parts of a salt represented by the above-mentioned formula (A7) in the form of oil. This is called as acid generator A7.

MS (ESI(+) Spectrum): M$^+$ 263.1
MS (ESI(−) Spectrum): M$^-$ 383.1

$^1$H-NMR (dimethylsulfoxide-$d_6$, Internal Standard: tetramethylsilane): δ (ppm) 1.30-2.08 (m, 5H), 2.63 (m, 1H), 2.87-2.94 (m, 2H), 3.90 (m, 1H), 4.15-4.45 (m, 4H), 7.70-7.90 (m, 15H)

Example 8

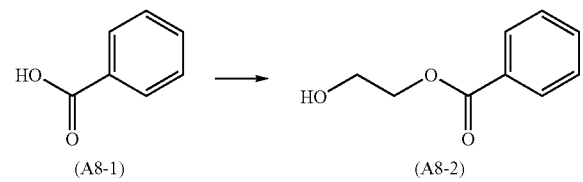

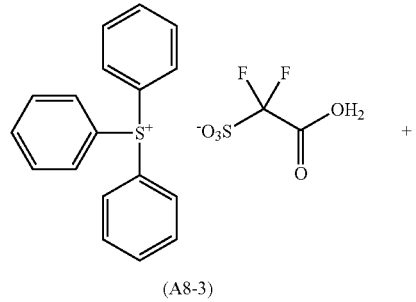

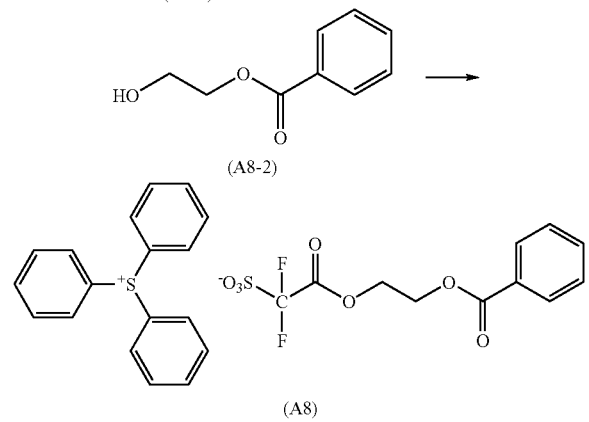

A mixture of 10.00 parts of a compound represented by the formula (A8-1), 50.83 parts of ethylene glycol and 0.40 part of sulfuric acid was stirred at 23° C. for 30 minutes. The obtained mixture was dehydrated for 1 hour with heating at 105° C., and then, cooled. To the mixture, 200 parts of ethyl acetate and 100 parts of ion-exchanged water were added and the obtained mixture was stirred at 23° C. for 30 minutes followed by conducting separation. The obtained organic layer was washed four times with ion-exchanged water and then, concentrated to obtain 13.10 parts of a compound represented by the formula (A8-2).

A mixture of 10.25 parts of a salt represented by the formula (A8-3), 50.00 parts of monochlorobenzene, 4.04 parts of the compound represented by the formula (A8-2) and 0.22 part of sulfuric acid was stirred at 23° C. for 30 minutes. The obtained mixture was dehydrated for 2 hours with heating at 135° C., and then, cooled. To the mixture, 100 parts of chloroform and 56 parts of ion-exchanged water were added, and the obtained mixture was stirred at 23° C. for 30 minutes followed by conducting separation. The obtained organic layer was washed six times with ion-exchanged water. The obtained organic layer was concentrated, and the obtained residue was mixed with 20.00 parts of acetonitrile. The obtained mixture was stirred at 23° C. for 30 minutes followed by concentration. The obtained residue was mixed with 30 parts of ethyl acetate and the supernatant solution was removed. The obtained residue was concentrated followed by mixing with 2.00 parts of acetonitrile and 20 parts of tert-butyl methyl ether. The supernatant solution was removed. The obtained residue was concentrated and mixed with 10 parts of ethyl acetate and the supernatant solution was removed. The obtained residue was mixed with 10 parts of tert-butyl methyl ether and supernatant solution was removed. The obtained residue was dissolved in chloroform, and the obtained solution was concentrated to obtain 5.75 parts of a salt represented by the above-mentioned formula (A8) in the form of oil. This is called as acid generator A8.

MS (ESI(+) Spectrum): M$^+$ 263.1

MS (ESI(−) Spectrum): M$^-$ 323.0

$^1$H-NMR (dimethylsulfoxide-$d_6$, Internal Standard: tetramethylsilane): δ (ppm) 4.42-4.61 (m, 4H), 7.25-8.00 (m, 20H)

Example 9

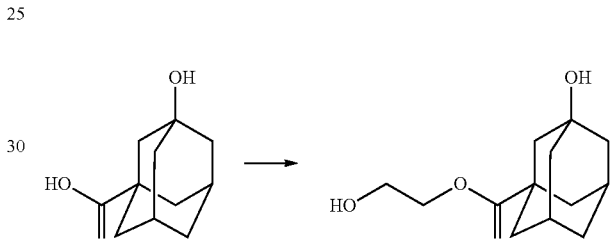

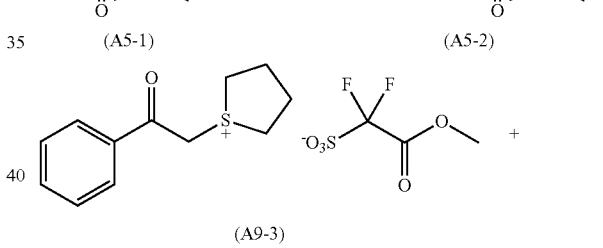

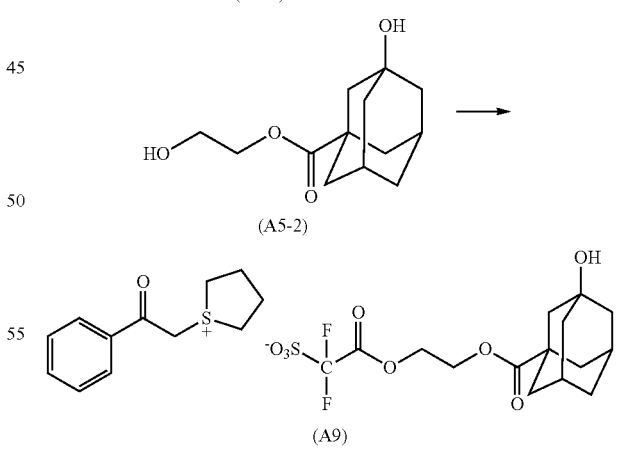

The reaction was conducted according to the same manner as that of Example 5, except that 4.36 parts of a salt represented by the formula (A9-3) was used in place of 4.98 parts of a salt represented by the formula (A5-3), to obtain 4.12 parts of a salt represented by the above-mentioned formula (A9). This is called as acid generator A9.

MS (ESI(+) Spectrum): M⁺ 207.1
MS (ESI(-) Spectrum): M⁻ 397.1

Example 10

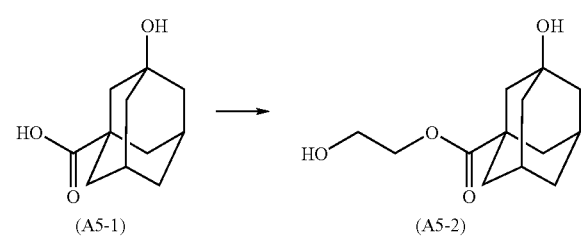

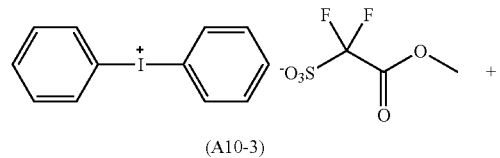

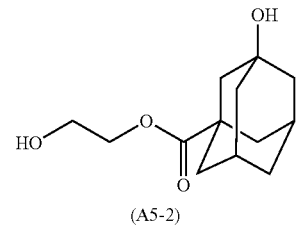

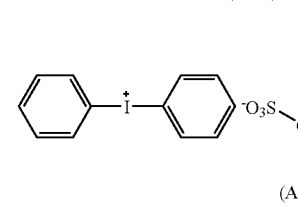

The reaction was conducted according to the same manner as that of Example 5, except that 5.18 parts of a salt represented by the formula (A10-3) was used in place of 4.98 parts of a salt represented by the formula (A5-3), to obtain 4.72 parts of a salt represented by the above-mentioned formula (A10). This is called as acid generator A10.

MS (ESI(+) Spectrum): M⁺ 281.0
MS (ESI(-) Spectrum): M⁻ 397.1

Example 11

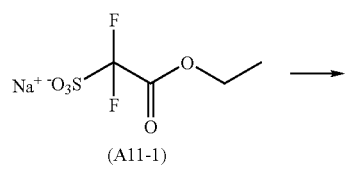

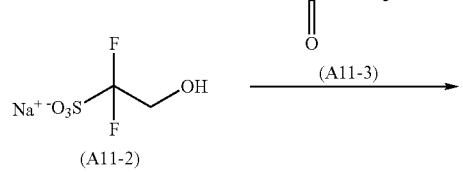

-continued

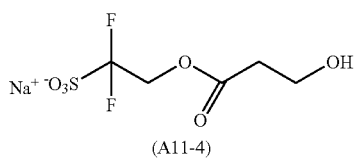

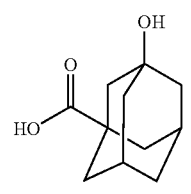

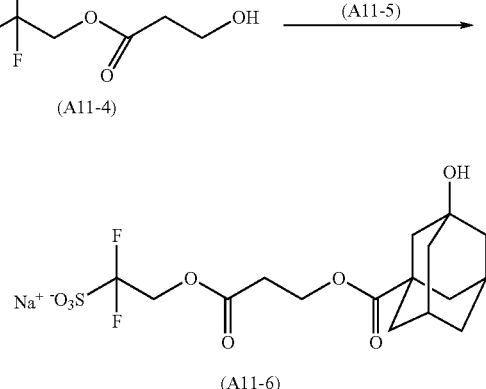

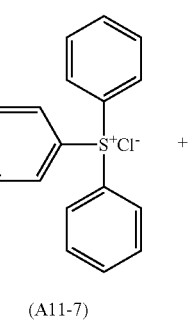

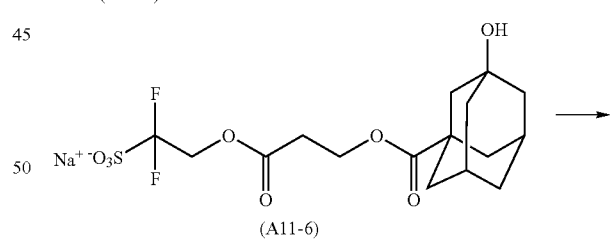

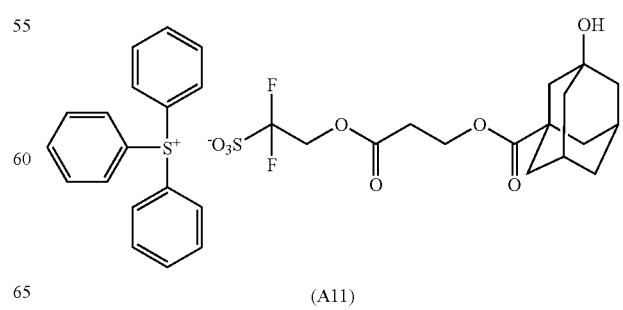

A mixture of 10.4 parts of lithium aluminum hydride and 120 parts of anhydrous tetrahydrofuran was stirred at 23° C. for 30 minutes. To the mixture, a solution prepared by dissolving 62.2 parts of a compound represented by the above-mentioned formula (A11-1) in 900 parts of anhydrous tetrahydrofuran was added dropwise in an ice bath, and the resultant mixture was stirred at 23° C. for 5 hours. To the obtained mixture, 50.0 parts of ethyl acetate and 50.00 parts of 6N hydrochloric acid were added and then the resultant mixture was stirred and separated to an organic layer and an aqueous layer. The obtained organic layer was concentrated and the obtained residue was purified with silica gel column (silica gel: Merck & Co., Inc., silica gel 60-200 mesh, Developing solvent: chloroform/methanol=5/1) to obtain 84.7 parts of a compound represented by the above-mentioned formula (A11-2). Purity: 60%.

A mixture of 1.61 parts of the compound represented by the above-mentioned formula (A11-3) and 75 parts of anhydrous tetrahydrofuran was stirred at 23° C. for 30 minutes. To the mixture, a solution of 2.89 parts of carbonyldiimidazole in 50 parts of anhydrous tetrahydrofuran was added dropwise at 23° C. and the resultant mixture was stirred at 23° C. for 4 hours. The obtained mixture was added dropwise to a mixture of 6.04 parts of the salt represented by the above-mentioned formula (A11-2) and 50 parts of anhydrous tetrahydrofuran at 54 to 60° C. over 25 minutes. The resultant mixture was heated at 65° C. for 18 hours, and then, cooled and filtrated. The obtained filtrate was concentrated and the obtained residue was purified with silica gel column (silica gel: Merck & Co., Inc., silica gel 60-200 mesh, Developing solvent: chloroform/methanol=5/1) to obtain 1.49 parts of a compound represented by the above-mentioned formula (A11-4).

A mixture of 1.49 parts of the compound represented by the above-mentioned formula (A11-4) and 50 parts of anhydrous tetrahydrofuran was stirred at 23° C. for 30 minutes. To the mixture, a solution of 0.95 part of carbonyldiimidazole in 25 parts of anhydrous tetrahydrofuran was added dropwise at 23° C. and the resultant mixture was stirred at 23° C. for 2 hours. The obtained mixture was added dropwise to a mixture of 1.14 parts of a compound represented by the above-mentioned formula (A11-5) and 20 parts of anhydrous tetrahydrofuran at 40° C. over 15 minutes. The resultant mixture was heated at 40° C. for 2 hours, and then, cooled and filtrated. The obtained filtrate was concentrated and the obtained residue was purified with silica gel column (silica gel: Merck & Co., Inc., silica gel 60-200 mesh, Developing solvent: chloroform/methanol=5/1) to obtain 2.12 parts of a compound represented by the above-mentioned formula (A11-6).

A mixture of 2.12 parts of the compound represented by the formula (A11-6), 10 parts of chloroform and 1.46 parts of the compound represented by the formula (A11-7) was stirred for 12 hours, and then washed with ion-exchanged water. To the obtained organic layer, 1.0 parts of active carbon was added to stir. The resultant mixture was filtrated and the obtained filtrate was concentrated. The obtained residue was mixed with 10 parts of ethyl acetate and the supernatant solution was removed. The obtained residue was mixed with 10 parts of tert-butyl methyl ether and the supernatant solution was removed. The obtained residue was dissolved in chloroform, and the obtained solution was concentrated to obtain 2.02 parts of a salt represented by the above-mentioned formula (A11). This is called as acid generator A11.

MS (ESI(+)) Spectrum): M$^+$ 263.1
MS (ESI(−)) Spectrum): M$^-$ 411.1

Resin Synthesis Example 1

Monomers used in this Example are following monomers B, C, D, E and F.

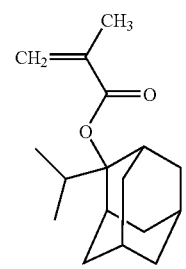

E

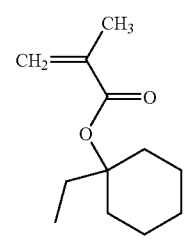

F

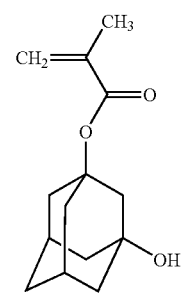

B

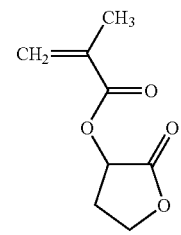

C

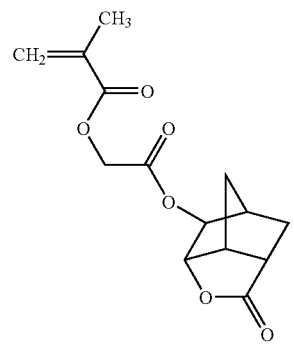

D

The monomers E, F, B, C and D were mixed in a molar ratio of 28/14/6/31/21 (monomer E/monomer F/monomer B/monomer C/monomer D), and 1,4-dioxane in 1.5 times part based on total parts of all monomers was added to prepare a mixture. To the mixture, azobisisobutyronitrile as an initiator in a ratio of 1 mol % based on all monomer molar amount and azobis (2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was repeated three times for purification. As a result, a resin having a weight-average molecular weight of about $8.5 \times 10^3$ was obtained in a yield of 74%. The resin had the following structural units. This is called as resin B1.

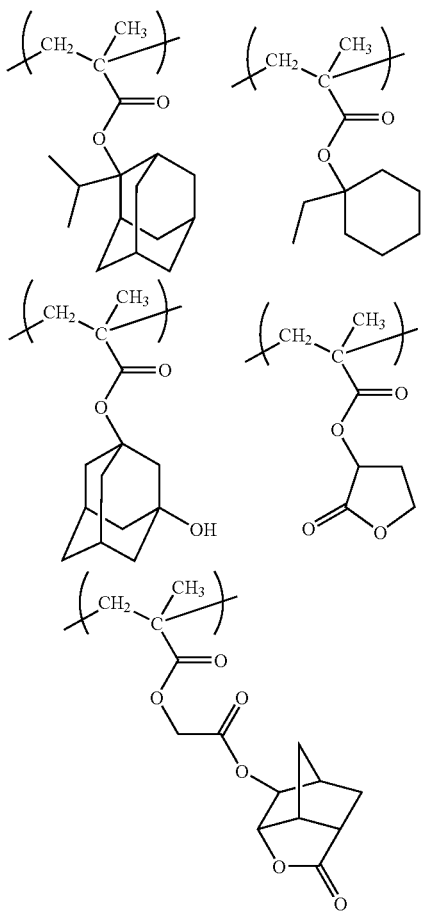

Resin Synthesis Example 2

Monomers used in this Example are following monomers A, H and G.

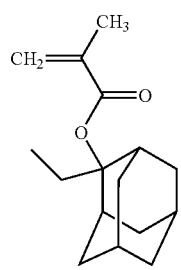

A

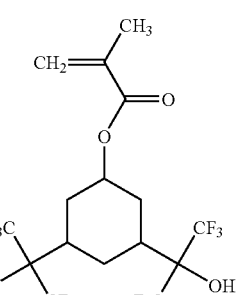

H

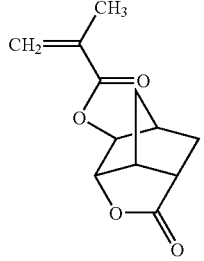

G

The monomers A, H and G were mixed in a molar ratio of 35/20/45 (monomer A/monomer H/monomer G), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 70° C. for about 5 hours. The reaction mixture obtained was poured into a mixture of a large amount of methanol and water to cause precipitation, and this operation was repeated three times for purification. As a result, a resin having a weight-average molecular weight of about $8.4 \times 10^3$ was obtained in a yield of 78%. The resin had the following structural units. This is called as resin B2.

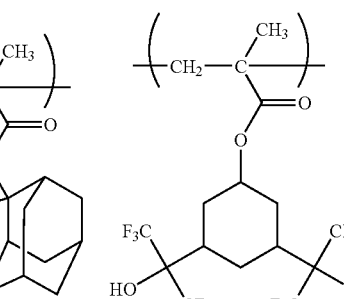

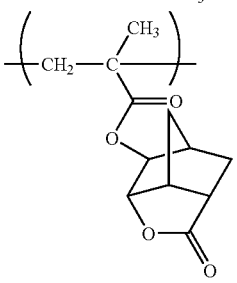

Examples 12 to 23 and Comparative Example 1

<Acid Generator>
Salt A1, A2, A3, A4, A5, A6, A7, A8, A9, A10, A11, C1 C1:

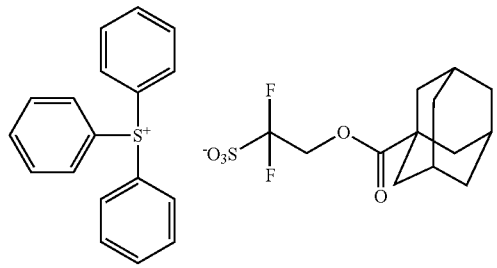

(C1)

<Resin>
Resin B1, B2
<Quencher>
Q1: 2,6-diisopropylaniline
<Solvent>

| Y1: | propylene glycol monomethyl ether | 20 parts |
|---|---|---|
| | propylene glycol monomethyl ether acetate | 265 parts |
| | γ-butyrolactone | 20 parts |

The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent (kind is described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 12 | B1/10 | A1/0.7 | Q1/0.065 | Y1 |
| Ex. 13 | B1/10 | A2/0.7 | Q1/0.065 | Y1 |
| Ex. 14 | B1/10 | A3/0.7 | Q1/0.065 | Y1 |
| Ex. 15 | B1/10 | A4/0.7 | Q1/0.065 | Y1 |
| Ex. 16 | B1/10 | A5/0.7 | Q1/0.065 | Y1 |
| Ex. 17 | B1/10 | A6/0.7 | Q1/0.065 | Y1 |
| Ex. 18 | B1/10 | A7/0.7 | Q1/0.065 | Y1 |
| Ex. 19 | B1/10 | A8/0.7 | Q1/0.065 | Y1 |
| Ex. 20 | B1/10 | A9/0.7 | Q1/0.065 | Y1 |
| Ex. 21 | B1/10 | A10/0.7 | Q1/0.065 | Y1 |
| Ex. 22 | B1/10 | A11/0.7 | Q1/0.065 | Y1 |
| Ex. 23 | B2/10 | A5/0.7 | Q1/0.065 | Y1 |
| Comp. Ex. 1 | B2/10 | C1/0.7 | Q1/0.065 | Y1 |

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at 95° C. for 60 seconds. Using an ArF excimer stepper ("FPA-5000AS3" manufactured by CANON INC., NA=0.75, ⅔ Annular), each wafer thus formed with the respective resist film was subjected to line and space pattern exposure, with the exposure quantity being varied stepwise.

After the exposure, each wafer was subjected to post-exposure baking on a hotplate at 95° C. for 60 seconds and then to paddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Line Edge Roughness (LER): The photoresist pattern was observed with a scanning electron microscope, and the difference between the height of the highest point and height of the lowest point of the scabrous wall surface of the photoresist pattern was measured. When the difference is 9 nm or less, LER is good and its evaluation is marked by "○", and when the difference is more than 9 nm, LER is bad and its evaluation is marked by "X". The smaller the difference is, the better the pattern is.

Focus margin (DOF): The photoresist patterns were obtained using 85 nm line and space pattern mask at the exposure amount where the line width of the line pattern and the space pattern became 85 nm, with the focal point distance being varied stepwise. Each of patterns were observed and the focal point distances wherein the patterns of which line width was in 85 nm±5% (about 80.8 to 89.3 nm) were obtained were measured and the difference between the maximum value of the focal point distance and the minimum value of the focal point distance was calculated. When the difference is 0.30 μm or more, DOF is good and its evaluation is marked by "○", and when the difference is less than 0.30 μm, DOF is bad and its evaluation is marked by "X".

TABLE 2

| Ex. No. | LER | DOF |
|---|---|---|
| Ex. 12 | ○ (6.64 nm) | ○ (0.45 μm) |
| Ex. 13 | ○ (6.96 nm) | ○ (0.45 μm) |
| Ex. 14 | ○ (6.88 nm) | ○ (0.60 μm) |
| Ex. 15 | ○ (5.88 nm) | ○ (0.60 μm) |
| Ex. 16 | ○ (5.28 nm) | ○ (0.90 μm) |
| Ex. 17 | ○ (6.48 nm) | ○ (0.45 μm) |
| Ex. 18 | ○ (5.42 nm) | ○ (0.75 μm) |
| EX. 19 | ○ (6.52 nm) | ○ (0.30 μm) |
| Ex. 20 | ○ (6.98 nm) | ○ (0.45 μm) |
| Ex. 21 | ○ (6.62 nm) | ○ (0.60 μm) |
| Ex. 22 | ○ (6.08 nm) | ○ (0.60 μm) |
| Ex. 23 | ○ (8.46 nm) | ○ (0.30 μm) |
| Comp. Ex. 1 | X (9.12 nm) | X (0.15 μm) |

The salt of the present invention is novel and is useful as an acid generator, and the photoresist composition containing the salt of the present invention provides a photoresist pattern having good LER and good DOF, and is especially suitable for ArF excimer laser lithography, KrF excimer laser lithography, ArF immersion lithography and EUV immersion lithography. Further, the photoresist composition of the present invention is also suitable for double imaging lithography.

What is claimed is:

1. A salt represented by the formula (a1):

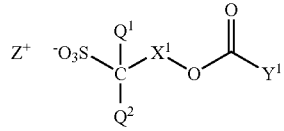
(a1)

wherein $Q^1$ and $Q^2$ each independently represent a fluorine atom or a C1-C4 perfluoroalkyl group, $X^1$ represents —CO—O—$X^{a1}$— or —$CH_2$—O—$X^{a2}$— wherein $X^{a1}$ and $X^{a2}$ independently each represent a C1-C15 alkylene group and one or more —$CH_2$— in the alkylene group can be replaced by —O— or —CO—, $Y^1$ represents a C3-C36 alicyclic hydrocarbon group or a C6-C24 aromatic hydrocarbon group, and the alicyclic hydrocarbon group and the aromatic hydrocarbon group can have one or more substituents, and one or more —$CH_2$— in the alicyclic hydrocarbon group can be replaced by —O— or —CO—, and $Z^+$ represents an organic cation.

2. The salt according to claim 1, wherein $Y^1$ represents a C3-C36 alicyclic hydrocarbon group or a C6-C24 aromatic hydrocarbon group, and one or more hydrogen atoms in the alicyclic hydrocarbon group and the aromatic hydrocarbon group can be replaced by a fluorine atom, a C1-C4 alkyl group, a C1-C4 fluorinated alkyl group, a hydroxyl group, a cyano group, a C2-C8 acyl group, a C2-C8 acyloxy group or a carboxyl group.

3. The salt according to claim 1, wherein $Y^1$ is a group represented by the formula ($Y^1$-1), ($Y^1$-2), ($Y^1$-3), ($Y^1$-4) or ($Y^1$-5):

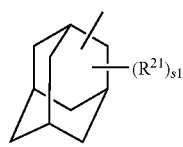
($Y^1$-1)

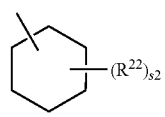
($Y^1$-2)

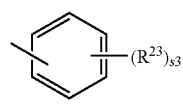
($Y^1$-3)

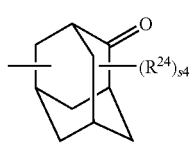
($Y^1$-4)

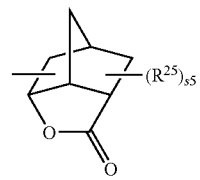
($Y^1$-5)

wherein $R^{21}$, $R^{22}$, $R^{23}$, $R^{24}$ and $R^{25}$ are independently in each occurrence a fluorine atom, a C1-C4 alkyl group, a C1-C4 fluorinated alkyl group, a hydroxyl group or a carboxyl group, and s1 represents an integer of 0 to 3, s2 represents an integer of 0 to 3, s3 represents an integer of 0 to 5, s4 represents an integer of 0 to 2, and s5 represents an integer of 0 to 2.

4. The salt according to claim 1, wherein $Z^+$ is a cation represented by the formula (IXa):

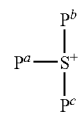
(IXa)

wherein $P^a$, $P^b$ and $P^c$ each independently represent a C1-C30 alkyl group, a C3-C30 alicyclic hydrocarbon group or a C6-C20 aromatic hydrocarbon group, and one or more hydrogen atoms in the alkyl group can be replaced by a hydroxyl group, a C1-C12 alkoxy group or a C3-C12 cyclic hydrocarbon group and one or more hydrogen atoms in the alicyclic hydrocarbon group can be replaced by a hydroxyl group, a C1-C12 alkyl group or a C1-C12 alkoxy group, and one or more hydrogen atoms in the aromatic hydrocarbon group can be replaced by a hydroxyl group, a C1-C12 alkyl group or a C1-C12 alkoxy group, or $P^a$ and $P^b$ are bonded each other to form a ring in which one or more —$CH_2$— can be replaced by —O—, —S—, —$SO_2$— or —CO—.

5. The salt according to claim 4, wherein $P^a$, $P^b$ and $P^c$ each independently represent a C6-C20 aromatic hydrocarbon group, and one or more hydrogen atoms in the aromatic hydrocarbon group can be replaced by a hydroxyl group, a C1-C12 alkyl group or a C1-C12 alkoxy group.

6. A photoresist composition comprising the salt according to claim 1 and a resin comprising a structural unit having an acid-labile group and being insoluble or poorly soluble in an aqueous alkali solution but becoming soluble in an aqueous alkali solution by the action of an acid.

7. The photoresist composition according to claim 6, wherein the photoresist composition further contains a basic compound.

8. A process for producing a photoresist pattern comprising the following steps (1) to (5):
(1) a step of applying the photoresist composition according to claim 6 or 7 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *